(12) United States Patent
Garreta et al.

(10) Patent No.: US 8,628,801 B2
(45) Date of Patent: Jan. 14, 2014

(54) PEGYLATED NANOPARTICLES

(75) Inventors: Juan Manuel Irache Garreta, Pamplona (ES); Krassimira Pavlova Yoncheva, Sofia (BG)

(73) Assignee: Universidad De Navarra, Pamplona (Navarra) (ES)

( * ) Notice: Subject to any disclaimer, the term of this patent is extended or adjusted under 35 U.S.C. 154(b) by 1344 days.

(21) Appl. No.: 11/568,454

(22) PCT Filed: Apr. 28, 2005

(86) PCT No.: PCT/ES2005/000226
§ 371 (c)(1),
(2), (4) Date: Dec. 4, 2006

(87) PCT Pub. No.: WO2005/104648
PCT Pub. Date: Nov. 10, 2005

(65) Prior Publication Data
US 2008/0248125 A1    Oct. 9, 2008

(30) Foreign Application Priority Data

Apr. 29, 2004 (ES) .................................. 200401022

(51) Int. Cl.
*A61K 9/14* (2006.01)
*C08F 222/06* (2006.01)
*A61K 8/81* (2006.01)

(52) U.S. Cl.
CPC ................ *A61K 9/14* (2013.01); *A61K 8/8164* (2013.01); *C08F 222/06* (2013.01); *Y10S 977/773* (2013.01)
USPC ............................ 424/489; 424/497; 977/773

(58) Field of Classification Search
None
See application file for complete search history.

(56) References Cited

U.S. PATENT DOCUMENTS

| | | | |
|---|---|---|---|
| 4,582,865 | A | 4/1986 | Balazs et al. |
| 4,904,479 | A | 2/1990 | Illum |
| 5,118,528 | A | 6/1992 | Fessi et al. |
| 5,578,325 | A | 11/1996 | Domb et al. |
| 5,962,566 | A | 10/1999 | Grandfils et al. |
| 6,066,340 | A | 5/2000 | Callegaro et al. |
| 6,132,750 | A | 10/2000 | Perrier et al. |
| 6,322,817 | B1 | 11/2001 | Maitra et al. |
| 6,383,478 | B1 | 5/2002 | Prokop et al. |
| 6,465,425 | B1 | 10/2002 | Tracy et al. |
| 6,660,810 | B1 | 12/2003 | Ferruti et al. |
| 2001/0053359 | A1 | 12/2001 | Watts et al. |
| 2002/0009493 | A1 | 1/2002 | Schwendeman et al. |
| 2002/0142041 | A1* | 10/2002 | Akiyama et al. ............... 424/486 |
| 2002/0155158 | A1* | 10/2002 | Lewis et al. .................... 424/486 |
| 2002/0197328 | A1 | 12/2002 | Kim et al. |
| 2003/0026844 | A1 | 2/2003 | Lee et al. |
| 2003/0059465 | A1 | 3/2003 | Unger et al. |
| 2005/0079222 | A1 | 4/2005 | Arbos Vila et al. |

FOREIGN PATENT DOCUMENTS

| | | |
|---|---|---|
| EP | 0 275 796 A1 | 7/1988 |
| EP | 0544259 A1 | 6/1993 |
| ES | 2098188 B1 | 4/1997 |
| ES | 2114502 B1 | 5/1998 |
| WO | 8903207 A1 | 4/1989 |
| WO | 9009401 A1 | 8/1990 |
| WO | 9606622 A1 | 3/1996 |
| WO | 9620698 A2 | 7/1996 |
| WO | 9704747 A1 | 2/1997 |
| WO | 9918934 A1 | 4/1999 |
| WO | 9947130 A1 | 9/1999 |
| WO | 0101964 A2 | 1/2001 |
| WO | 0128602 A1 | 4/2001 |
| WO | 0182724 A2 | 11/2001 |
| WO | 0230990 A1 | 4/2002 |
| WO | 2004009060 A1 | 1/2004 |
| WO | WO 2005/014648 | 11/2005 |
| WO | WO 2005/105056 | 11/2005 |

OTHER PUBLICATIONS

H Otsuka, Y Nagasaki, K Kataoka. "PEGylated Nanoparticles for Biological and Pharmaceutical Applications." Advanced Drug Delivery Reviews 55 (2003) 403-419.*
H Otsuka, Y Nagasaki, T Okano, K Kataoka. "Functionalization of Polylactide(PLA) Surface Using Heterobifunctional PEG/PLA Block Copolymers for the Control of Cell Behavior at Surfaces." Proceedings of the $22^{nd}$ Annual EMBS International Conference, Jul. 23-28, 2000, Chicago IL.*
PJ Photos, L Bacakova, B Discher, FS Bates, DE Discher. "Polymer Vesicles in Vivo: Correlations with PEG Molecular Weight." Journal of Controlled Release 90 (2003) 323-334.*

(Continued)

*Primary Examiner* — Frederick Krass
*Assistant Examiner* — Isaac Shomer
(74) *Attorney, Agent, or Firm* — Hultquist PLLC; Steven J. Hultquist; Mary B. Grant

(57) ABSTRACT

The present invention relates to nanoparticles comprising a biodegradable polymer, preferably the vinyl methyl ether and maleic anhydride (PVM/MA) copolymer, and a polyethylene glycol or derivatives thereof. These nanoparticles are easy to produce and provide excellent bioadhesion, size and zeta potential characteristics making them suitable for the administration of active molecules. The selection of the type of polyethylene glycol used in their production allows suitably modulating the characteristics of these nanoparticles, which can be advantageously used according to the type of drug to be carried and/or the method of administration of the pharmaceutical formulation. pegylation is carried out by simple incubation for a short time period of the two macromolecules in question, without needing to have to resort to the use of organic solvents with high toxicity or long and laborious organic synthesis processes. Furthermore, the pegylation process can be associated to the process of encapsulating the biologically active molecule.

18 Claims, 12 Drawing Sheets

(56) References Cited

OTHER PUBLICATIONS

P Arbos, MA Campanero, MA Arangoa, MJ Renedo, JM Irache. "Influence of the surface characteristics of PVM/MA Nanoparrticles on their bioadhesive properties." Journal of Controlled Release, vol. 89, 2003, pp. 19-30.*

NV Efremova, Y Huang, NA Peppas, DE Leckband. "Direct Measurement of Interactions between Tethered Poly(ethylene glycol) Chains and Adsorbed Mucin Layers." Langmuir, vol. 18, 2002, pp. 836-845.*

K Yoncheva, E Lizarraga, JM Irache. "Pegylated nanoparticles based on poly(methyl vinyl ether-co-maleic anhydride): preparation and evaluation of their bioadhesive properties." European Journal of Pharmaceutical Sciences, vol. 24, 2005, pp. 411-419.*

Benedetti, L.M., et al, "Microspheres of hyaluronic acid esters Fabrication methods and in vitro hydrocortisone release", "J. Control. Rel.", Jul. 1990, pp. 33-41, vol. 13, No. 1.

Blanco, M.D., et al., "Development and characterization of protein-loaded poly(lactide-co-glycolide) nanospheres", "Eur. J. Pharm. Biopharm.", Jun. 1997, pp. 287-294, vol. 43, No. 3.

Blanco, Dolores, et al., "Protein encapsulation and release from poly(lactide-co-glycolide) microspheres: effect of the protein and polymer properties of the co-encapsulation of the surfactants", "Eur. J. Pharm. Biopharm.", May 1998, pp. 285-294, vol. 45, No. 3.

Hawley, Ann E., et al., "Lymph node localisation of biodegradable nanospheres surface modified with poloxamer and poloxamine block co-polymers", "FEBS Letters", Jan. 6, 1997, pp. 319-323, vol. 400, No. 3.

Kabanov, Alexander V., et al., "Pluronic block copolymers as modulators of drug efflux transporter activity in the blood-brain barrier ", "Adv. Drug Deliv. Rev.", Jan. 21, 2003, pp. 151-164, vol. 55, No. 1.

Lemieux, P., et al, "A combination of poloxamers increases gene expression of plasmid DNA in skeletal muscle", "Gene Therapy", Jun. 2000, pp. 986-991, vol. 7, No. 11.

Lim, S.T., et al., "Preparation and evaluation of the in vitro drug release properties and mucoadhesion of novel microspheres of hyaluronic acid and chitosan", "J. Control. Rel.", May 15, 2000, pp. 281-292, vol. 66, No. 2-3.

Lim, S.T., et al., "In vivo evaluation of novel hyaluronan/chitosan microparticulate delivery systems for the nasal delivery of gentamicin i", "Int. J. Pharm.", Jan. 1, 2002, pp. 73-82, vol. 231, No. 1.

Lourenco, Christina, et al., "Steric stabilization of nanoparticles: Size and surface properties", "Int. J. Pharm.", Jul. 12, 1996, pp. 1-12, vol. 138, No. 1.

Moghimi, S.M., et al., "Surface engineered nanospheres with enhanced drainage into lymphatics and uptake by macrophages of the regional lymph nodes", "FEBS Letters", May 9, 1994, pp. 25-30, vol. 344, No. 1.

Sanchez, Alejandro, et al., "Development of biodegradable microspheres and nanospheres for the controlled release of cyclosporin A", "Int. J. Pharm.", Oct. 15, 1993, pp. 263-273, vol. 99, No. 2-3.

Sanchez, Alejandro, et al., "Biodegradable micro- and nanoparticles as long-term delivery vehicles for interferon-alpha", "Eur. J. Pharm. Sci.", Mar. 2003, pp. 221-229, vol. 18, No. 3-4.

Tobio, Maria, et al., "A Novel System Based on a Poloxamer/ PLGA Blend as a Tetanus Toxoid Delivery Vehicle", "Pharm. Res.", May 1999, pp. 682-688, vol. 16, No. 5.

Yoncheva, K. et al., "Peglated nanoarticles based on poly(methyvinyl ether-co-maleic anhydrude): preparation and evaluation of their bioadhesive properties", *Eur. J. Pharm. Sci.*, 24:5 (2005), pp. 411-419.

Chiellini, E., et al., "Design of polymeric systems for targeted administration of peptide and protein drugs", *Polymer Preprints*, 39:2(1998), pp. 182-183.

Arbos, P., et al., "Gantrez® AN as a new polymer for the preparation of ligand-nanoparticle conjugates", *Journal of Controlled Release*, 83:3 (2002), pp. 321-330.

Arbos, P. et al., "Quantification of the bioadhesive properties of protein-coated PVM/MA nanoparticles", *International Journal of Pharmaceutics*, 242:1-2 (2002), pp. 129-136.

Gref, R., et al., "The controlled intravenous delivery of drugs using PEG-coated sterically stabilized nanospheres," Advanced Drug Delivery Reviews 16 (1995) 215-233.

Lai, S. et al. , "Rapid transport of large polymeric nanoparticles in fresh undiluted human mucus", PNAS, Jan. 30, 2007, pp. 1482-1487, vol. 104, No. 5.

Wang, Y. et al. , "Addressing the PEG Mucoadhesivity Paradox to Engineer Nanoparticles that Slip through the Human Mucus Barrier", "Angew Chem Int Ed Engl.", 2008, pp. 9726-9729, vol. 47, No. 50.

Yoncheva, K. et al. , "Evaluation of bioadhesive potential and intestinal transport of pegylated poly(anhydride) nanoparticles", Int'l Journal of Pharmaceutics, 2007, pp. 156-165, vol. 334.

* cited by examiner

PEGYLATED NANOPARTICLES

CROSS-REFERENCE TO RELATED APPLICATIONS

This application is filed under the provisions of 35 U.S.C. §371 and claims the benefit of priority of International Patent Application No. PCT/ES2005/000226, filed Apr. 28, 2005, which in turn claims priority of Spanish Patent Application No. P 200401022, filed Apr. 29, 2004. The disclosures of all said applications are hereby incorporated herein by reference in their respective entireties.

FIELD OF THE INVENTION

The invention relates to pegylated nanoparticles based on a biodegradable polymer and a polyethylene glycol, with process for manufacturing same with formulations containing them and their use as drug administration systems.

BACKGROUND OF THE INVENTION

In recent years biodegradable polymeric nanoparticles have been proposed as new drug administration systems. One of the most important features that they offer is the controlled release of the incorporated drug. This leads to greater therapeutic efficacy, provides a more comfortable administration for the patient and allows preventing overdose. Furthermore, drugs with different physicochemical features can be included, enabling improving their stability in biological fluids. This fact is very important in the case of antigens, proteins and macromolecules in general. Furthermore due to their small size, nanoparticles are suitable for the administration of drugs through various routes, such as orally, parenterally and ocularly (Kreuter, Adv. Drug Del. Rev., 7 (1991) 71-86; Gref et al., Science, 263 (1994) 1600-1603; Zimmer and Kreuter, Adv. Drug Del. Rev., 16 (1995) 61-73).

Oral administration is the most convenient and popular route for the administration of drugs. However, the bioavailability of a certain active molecule depends (i) on the characteristics of the molecule of the drug and on the pharmaceutical form and (ii) on the physiological conditions present in the gastrointestinal tract, such as the presence of proteolytic enzymes, peristaltic movements and presystemic metabolism. Colloidal systems such as nanoparticles have been proposed to overcome some of these obstacles. These carriers essentially have a large specific surface whereby their interaction with the biological support (gastrointestinal mucosa) is facilitated. The drug release control also allows prolonging over time the effect of molecules with low biological half-lives. On the other hand, nanoparticles can be uptaken by Peyer's patch cells and by lymphoid tissue follicles (Hodges et al., J. Drug Target., 3 (1995) 57-60; Florence, Pharm. Res., 14 (1997) 259-266). This phenomenon allows directing the drug towards the lymphatic pathway, and in the case of vaccines facilitating their antigen presentation. However, conventional nanoparticles have several significant drawbacks with respect to their use by oral administration: (i) certain instability in gastrointestinal fluids, (ii) a low degree of intestinal absorption, and (iii) non-specific tropism or adhesion in the gastrointestinal mucosa.

Parenteral administration of nanoparticles provides controlled systemic release that is suitable for drugs with (i) low oral bioavailability, (ii) short biological plasma half-life and (iii) limited stability. Another significant advantage of parenteral nanoparticles is the possibility of concentrating the drug in a certain organ. However, nanoparticles are quickly recognized, uptaken and eliminated from the blood circulation by macrophages of the mononuclear phagocyte system (MPS) after their intravenous administration. This phenomenon limits their function in controlled release as well as the possibility of concentrating the drug in tissues other then MPS.

Ophthalmic administration of controlled release systems has significant advantages for the treatment of ocular diseases, although a systemic effect may also be obtained. However, ocular administration is associated to the quick elimination of the formulation from the precorneal area due to draining towards the nasolacrimal duct and lacrimal dilution. These processes give rise to the fact that a very low percentage of the administered drug may penetrate the cornea and reach intraocular tissues (less than 5%). This draining is responsible for the occurrence of systemic effects upon administering the formulation through this route. A number of studies have demonstrated that the use of nanoparticles allows increasing the amount of the drug in the conjunctiva and increasing their bioavailability compared with conventional ophthalmic forms such as solutions and ointments (Gurny et al., J. Controlled Rel., 6 (1987) 367-373; Deshpande et al., Crit. Rev. Ther. Drug Carrier Syst., 15 (1998) 381-420). Colloidal systems can be administered as simple drops avoiding vision problems due to their low viscosity. The frequency of use may be reduced due to the sustained release of the drug from the matrix of the nanoparticles. However, nanoparticles also show a quick elimination from the absorption site.

Therefore, even though nanoparticles are potentially useful for the various previously mentioned administration methods, there are still problems which make their use difficult. Modification of the characteristics of the polymeric matrix as well as of their surface may provide the solution to some of the problems described above.

From this point of view, the association or coating of nanoparticles with suitable polymers may modify their physicochemical characteristics, and it may indirectly modify their distribution and interaction with the biological medium. A possible strategy is polyethylene glycol (PEG) binding to the nanoparticles, known as pegylation or obtaining stealthy nanoparticles.

With respect to their use by oral administration, the association of polyethylene glycols to conventional nanoparticles allows protecting them against enzymatic attack in digestive fluids. This is because of the potential of polyethylene glycols to reject proteins (Gref et al., Science, 263 (1994) 1600-1603). This strategy would also allow minimizing their interaction with mucin and other proteins present in the lumen. A similar strategy has been applied to the development of the nanoparticles for ocular use. Fresta et al. observed a significant increase of the ocular absorption of acyclovir after its administration in poly(alkylcyanoacrylate) nanospheres coated with polyethylene glycol (Fresta et al., J. Pharm. Sci., 90 (2001) 288-297). This phenomenon is explained by a greater interaction of the coated nanoparticles with the corneal epithelium.

Various nanoparticles coated with polyethylene glycol administered intravenously have demonstrated prolonged circulation (Gref et al., Science, 263 (1994) 1600-1603; Stolnik et al., Pharm. Res., 11 (1994) 1800-1808; Bazile et al., J. Pharm. Sci., 84 (1995) 493-498). Poly(lactic) (PLA) nanoparticles coated with polyethylene glycol have a much longer plasma half-life ($t\frac{1}{2}$=6 h) than when they are coated with albumin or poloxamer ($t\frac{1}{2}$=2-3 minutes) (Verrecchia et al., J. Controlled Rel., 36 (1995) 49-61). The presence of hydrophilic polyethylene glycol chains on the surface of the nanoparticles significantly reduces their interaction with blood proteins (known as opsonins). These proteins promote phagocytosis forming a "bridge" between the particles and phagocytes (Frank & Fries, Immunol. Today, 12 (1991) 322-326). However, the hydrophilic properties of polyethylene glycols are not the only important factor providing efficient resistance to opsonization. Other hydrophilic polymers such as polyvinyl alcohol have demonstrated a low protecting ability against opsonization of the nanoparticles (Leroux et al., Life Sci., 57 (1995) 695-703). Therefore, the steric stabilization provided by pegylation would also be due to other physicochemical properties, such as the high flexibility of the PEG chains and a specific structural formation (Mosquiera et al., Biomaterials, 22 (2001) 2967-2979).

The main drawback with this new strategy is the stability of the association of polyethylene glycols to the surface of the nanoparticles (Peracchia et al., Life Sci., 61 (1997) 749-761). It is known that the ability of polyethylene glycol to reject proteins depends on the configuration, the charge, the length and the flexibility of the chains (Torchillin, J. Microencaps., 15 (1998) 1-19). The process for modifying the surface of the nanoparticles is mainly carried out by physical adsorption (Stolnik et al., Adv. Drug Del. Rev., 16 (1995) 195-214) or by covalent bonding (De Jaeghere et al., J. Drug Target., 8 (2000) 143-153). However, the drawback of simple adsorption is the quick loss of the coating due to the instability of the interaction. Given that covalent binding is preferable, most pegylated nanoparticles have been prepared using polyethylene glycol copolymers with lactic or glycolic acid. However, the copolymerization process requires the use of several catalysts and specific chemical conditions (Beletsi et al., Int. J. Pharm., 182 (1999) 187-197). Furthermore, the toxic organic solvent residues used in the organic synthesis (methylene chloride, toluene etc.), may be problematic.

Therefore, it is still necessary to obtain nanoparticles which are stable in oral administration, which maintain the hydrophilic coating and which have good bioadhesive characteristics and specificity in the gastrointestinal tract. They must be non-toxic, biodegradable and easy to produce in order to be effective.

SUMMARY OF THE INVENTION

The object of the present invention is to provide nanoparticles which resolve the previously mentioned drawbacks, i.e. they have stability and specificity in oral administration, they have good bioadhesive characteristics for interacting with mucosae, they are capable of carrying a wide range of active molecules, they release the active molecule in a controlled manner and prevent its elimination from the blood system, especially when they are parenterally administered.

It has been observed that nanoparticles formed by a biodegradable polymer and polyethylene glycol resolve these problems. It has especially been found that nanoparticles formed by a polyvinyl methyl ether and maleic anhydride and polyethylene glycol copolymer are easy to produce and provide excellent bioadhesion, size and zeta potential characteristics making them suitable for the administration of active molecules. It has further been found that the selection of the type of polyethylene glycol used to produce them allows suitably modulating the features of these nanoparticles, which can be advantageously used according to the type of drug to be carried and/or the method of administration of the pharmaceutical formulation.

Therefore, in a first aspect the invention relates to pegylated nanoparticles for carrying biologically active molecules comprising a biodegradable polymer and a polyethylene glycol or derivatives thereof. In one variant, the biodegradable polymer is a vinyl methyl ether and maleic anhydride (PVM/MA) copolymer.

The polyethylene glycol preferably has a molecular weight comprised between 400 and 35,000 Da. Polyalkylene glycol provides good results when it is selected from the group of polyethylene glycols, polypropylene glycols, block or random copolymers including the two types of units, mixtures thereof or derivatives thereof. At least one terminal hydroxyl group of the polyethylene glycol is optionally substituted, preferably with an alkoxy, acrylate, methacrylate, alkyl, amino, phosphate, isothiocyanate, sulfhydryl, mercapto or sulfate group.

In one variant of the invention, the weight ratio between polyethylene glycol and the biodegradable polymer is 1:2-6, preferably 1:2-4, more preferably about 1:4.

The pegylated nanoparticles of the invention may incorporate an active molecule, such as proteins, peptides, DNA, RNA, nucleosides, nucleotides, oligonucleotides or polynucleotides. In terms of their activity, it may be an anti-tumor agent or an antigen for tumors, or a protective agent of the central nervous system or a glucocorticoid, or an antigen for vaccination or an allergen for immunotherapy, among others.

In another aspect, the invention relates to a pharmaceutical composition comprising pegylated nanoparticles as described above. In one variant the formulation is for oral administration. In another variant, it is for parenteral administration or for administration through mucosa (for example ophthalmic mucosa).

Therefore, the pegylated nanoparticles of the invention can be used in the manufacture of a medicament. It can optionally be in lyophilized form.

In another aspect the invention relates to a process for preparing pegylated nanoparticles which are described and comprising the step of simultaneous incubation of the polymer and the polyethylene glycol in an organic solvent, prior to desolvating the polymer with a hydroalcoholic solution. In one variant the concentration of the biodegradable polymer is comprised between 0.001 and 10% w/v and the concentration of polyethylene glycol between 0.001 and 5% w/v. The organic phase/hydroalcoholic solution phase ratio is optionally comprised in the range between 1/1-1/10.

The process may further comprise additional steps for eliminating the organic solvents and/or purification, as well as steps for stabilizing the pegylated nanoparticles by means of the use of cross-linking agents. The biologically active molecule can be incorporated in the step of simultaneous incubation of the polymer and the polyethylene glycol in an organic solvent, or can subsequently be incorporated in the aqueous suspension of the already formed nanoparticles so that their association can occur.

DETAILED DESCRIPTION OF THE INVENTION

Figure 1:
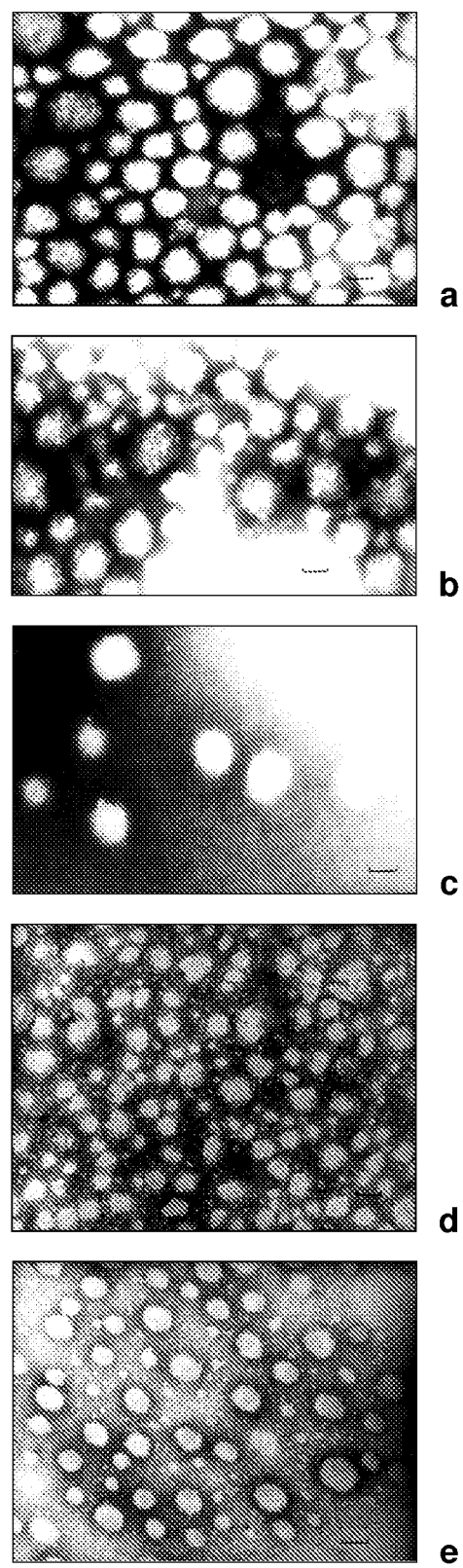
FIG. 1 shows transmission electron microscopy (TEM) photographs of the different types of nanoparticles—(a) NP; (b) PEG NP; (c) mPEG NP; (d) DAE-PEG NP; (e) DAP-PEG NP. The scale presents 150 nm.

It has surprisingly been found that the modification and coating of the nanoparticles of a biodegradable polymer such as vinyl methyl ether and maleic anhydride (PVM/MA) copolymer with different polyethylene glycols allows obtaining nanoparticles with physicochemical, bioadhesion and specificity characteristics in oral administration converting them in very interesting systems as special drug carriers. The features of these nanoparticles can advantageously be modulated according to the type of polyethylene glycol used and the preparation process. The pegylated nanoparticles of the invention can prolong the residence time in the mucosa after their oral or ocular administration. These nanoparticles are interesting for the administration of drugs with narrow absorption windows and thus improve their bioavailability.

These nanoparticles are also suitable vectors for drugs with elevated toxicity (for example cytostatic drugs) as they allow an increase in the plasma circulation time of the system during which time the drug is gradually released in a controlled manner. On the other hand, pegylated nanoparticles can prevent the recognition and elimination by means of mononuclear phagocyte system (MPS) cells, providing a prolonged circulation of drugs after their intravenous administration.

The term "nanoparticles" is used to designate spheres or similar shapes with a size less than 1.0 micrometer, preferably in the range of 10 to 900 nanometers.

As mentioned above, in one aspect the invention relates to pegylated nanoparticles formed from a biodegradable polymer. Biodegradable polymers known in the state of the art which give rise to the formation of nanoparticles can be used. These polymers include, among others, polyhydroxy acids such as polylactic and polyglycolic acid and copolymers thereof (for example PLGA), polyanhydrides, polyesters and polysaccharides, for example chitosan. The term "biodegradable" in this description refers to polymers which dissolve or degrade in a period of time which is acceptable for the desired application, in this case in vivo therapy, once they are exposed to a physiological solution of pH 6-9 and a temperature comprised between 25° C. and 40° C.

In one variant of the invention vinyl methyl ether and maleic anhydride copolymer in anhydride form (PVM/MA or Gantrez AN) is used as the biodegradable polymer. It preferably has a molecular weight comprised between 100 and 2400 KDa, more preferably between 200 and 2000 KDa. In one variant of the invention a PVM/MA copolymer with a molecular weight between 180 and 250 KDa is preferred.

This copolymer is advantageous because it is widely used in pharmaceutical technology due to its low toxicity (LD 50=8-9 g/kg orally) and excellent biocompatibility. It is also easy to obtain in terms of quantity and its price. This polymer can react with different hydrophilic substances due to its anhydride groups without having to resort to the usual organic reagents (glutaraldehyde and carbodiimide derivatives) having a significant toxicity (Arbos et al., J. Controlled Rel., 83 (2002) 321-330). The polymer is insoluble in an aqueous medium, but the anhydride group of the Gantrez AN hydrolyzes, giving rise to obtaining carboxylic groups. Dissolution is slow and depends on the conditions in which it occurs. Due to the bioavailability of functional groups in PVM/MA, the covalent binding of molecules with nucleophilic groups, such as hydroxyls (—OH) or amines (—NH$_2$), occurs by simple incubation in an aqueous medium.

Non-pegylated nanoparticles of this copolymer and their preparation are described in WO 02/069938 belonging to the same applicant, and the content of this application is herein fully incorporated by reference. The vinyl methyl ether and maleic anhydride copolymer nanoparticles are easily prepared by desolvating the polymer by means of adding to an organic solution thereof a first polar solvent (miscible with a solution of the polymer) and subsequently adding a second non-solvent liquid, in this case a hydroalcoholic solution. A cross-linking agent can optionally be added. Obtaining pegylated nanoparticles of this polymer is described below and it has been found that they are very easy to obtain.

In the present description, the term "polyethylene glycol" is understood to be any hydrophilic polymer soluble in water containing ether groups linked by 2 or 3 carbon atom, optionally branched alkylene groups. Therefore this definition includes branched or non-branched polyethylene glycols, polypropylene glycols, and also block or random copolymers including the two types of units. The term also includes derivatives of the terminal hydroxyl groups, which can be modified (1 or both ends) so as to introduce alkoxy, acrylate, methacrylate, alkyl, amino, phosphate, isothiocyanate, sulfhydryl, mercapto and sulfate groups. The polyethylene glycol or polypropylene glycol can have substituents in the alkylene groups. If they are present, these substituents are preferably alkyl groups.

Polyethylene glycols are water-soluble polymers that have been approved for the oral, parenteral and topical administration of drugs (FDA). Polyethylene glycols are produced by means of polymerization of ethylene oxide (EO) or propylene oxide (PO) in the presence of water, monoethylene glycol or diethylene glycol as reaction initiators in an alkaline medium (1,2-Epoxide Polymers: Ethylene Oxide Polymers and Copolymers" in Encyclopedia of Polymer Science and Engineering; Mark, H. F. (Ed.), John Wiley and Sons Inc., 1986, pp. 225-273). When the desired molecular weight (generally controlled by means of in-process measurements of viscosity) is reached, the polymerization reaction ends by neutralizing the catalyst with an acid (lactic acid, acetic acid or the like). The result is a linear polymer having a very simple structure:

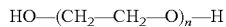

$$HO-(CH_2-CH_2-O)_n-H$$

where (n) is the number of EO monomers or units. The units alternatively contain propylene groups.

Although technically all these products should be called poly(oxyalkylenes), products with mean molecular weights (or molecular mass) between 200 and 35,000 are known as polyethylene glycols (PEGs). This term polyethylene glycol is normally used to indicate the significant influence of hydroxyl terminal groups on the physicochemical properties of these molecules. The term PEG is normally used in combination with a numerical value. In the pharmaceutical industry the number indicates the mean molecular weight, whereas in the cosmetic industry the number accompanying the letters PEG refers to the polymerized EO units forming the molecule (Hand book of Pharmaceutical Excipients, Rowev R. C., Sheskey P. J., Weller P. J. (Eds.), 4$^{th}$ Edition, Pharmaceutical Press and American Pharmaceutical Association, London, UK, 2003). PEGs are included in various pharmacopeias, although the nomenclature differs (International Harmonisation: Polyethylene glycol (PEG): Pharmeuropa 1999, 11, 612-614). According to the Handbook of Pharmaceutical Excipients (Fourth Edition), 2003 Edited by R. C. Rowe, P. J. Sheskey and P. J. Weller Published by the Pharmaceutical Press (London, UK) and the American Pharmaceutical Association (Washington, USA), polyoxyethylene glycols are also referred to as polyethylene glycols, macrogols, macrogol or PEG. The British Pharmacopoeia uses polyethylene glycols and macrogols, the Ph Eur polyethylene glycols and macrogol while the US pharmacopoeia (USP) uses polyethylene glycol(s).

PEGs with molecular weight less than 400 are non-volatile liquids at room temperature. PEG 600 shows a melting point comprised between 17 and 22° C., whereas PEGs with mean molecular weights comprised between 800 and 2000 are pasty materials with low melting points. Above a molecular weight exceeding 3000, PEGs are solid and up to PEG 35000 is commercially available. On the other hand, although the melting point of PEGs increases when the molecular weight increases, the boiling point increases up to a maximum value of 60° C. Likewise, when the molecular weight increases, its aqueous solubility decreases. In any case for PEG 35000, an amount close to 50% m/m can be dissolved in water.

From a toxicological point of view, PEGs are considered rather non-toxic and non-immunogenic (Hermansky S. J et al., Food Chem. Toxic., 1995, 33, 139-140; Final Report on the Safety Assessment of PEGs: J. A. C. T., 1993, 12, 429-457; Polyethylene glycol, 21 CFR 172.820, FDA). The allowable daily intake defined by the WHO is 10 mg/kg weight (Polyethylene glycols; Twenty-third report of the Joint FAO/WHO Expert Committee on Food Additives; World Health Organisation, Geneva; Technical Report Series 1980, 648, 17-18).

Polyethylene glycol derivatives have advantages that are similar to traditional PEGs such as their aqueous solubility, physiological inactivity, low toxicity and stability under very different conditions. These derivatives include very different products and are characterized by the functional group substituting the hydroxyl, such as —NH2 (among the most reactive ones), phenol, aldehyde, isothiocyanate, —SH groups, etc. The following can be pointed out among the polyethylene glycol derivatives that can be used in the invention:

Polyoxyethylene esters: PEG monomethyl ether monosuccinimidyl succinate ester; PEG monomethyl ether monocarboxymethyl ether; PEG adipate; PEG distearate; PEG monostearate; PEG hydroxystearate; PEG dilaurate; PEG dioleate, PEG monooleate, PEG monoricinoleate; PEG coconut oil esters.

Polyoxyethylene alkyl ethers: PEG monomethyl ether or methoxy PEG (mPEG); PEG dimethyl ether.

Others: Poly(ethylene glycol terephthalate); polyoxyethylene derivatives and sorbitan esters and fatty acids; ethylene oxide and propylene oxide copolymers; ethylene oxide with acrylamide copolymers.

PEG derivatives: O,O'-Bis-(2-aminoethyl)polyethylene glycol (DAE-PEG 2000); O,O'-Bis-(2-aminopropyl) polypropylene glycol-polyethylene glycol-polypropylene glycol.

In one variant of the invention the polyethylene glycol is not branched and does not have substituted hydroxyl groups. In this variant the polyethylene glycols used preferably have a molecular weight between 400 and 35,000 Da. When the molecular weight is less than 400 Da it has been found that pegylation does not efficiently occur. Therefore in one preferred variant of the invention the polyethylene glycol used in manufacturing pegylated nanoparticles has a molecular weight equal to or greater than 400, more preferably equal to or greater than 1000, values between 1500 and 10,000 are especially preferred, preferably between 2000 and 5000 KDa.

Therefore, in one variant of the invention polyethylene glycol 2000 (PEG 2000) is used. The amount PEG 2000 with respect to the polymer is preferably from 1:2-6, values close to a 1:4 ratio provide good results. For example about 0.25 mg PEG 2000/mg polymer provides efficient pegylation. In this case, the amount associated to the nanoparticles is about 55.0 micrograms per mg nanoparticle. These nanoparticles are characterized by having a spherical shape and a size close to 300 nm.

In another variant of the invention the polyethylene glycol used in manufacturing pegylated nanoparticles has a blocked terminal hydroxyl group, for example by means of a methyl ether derivative. This reduces its hydrophilia and can even change the structure of the nanoparticle. In this case, a greater percentage of the polyethylene glycol chains would be included inside it and only a small part thereof would be located on the surface of the nanoparticles. This particularity allows us to modulating the features of the nanoparticles by means of blocking the hydroxyl groups or by introducing other functional groups as described below. In the case of m-PEG, which is inside the nanoparticles, its function would be to modify the release of the drug by modifying the porosity of the polymeric matrix.

Polyethylene glycol methyl ether 2000 (mPEG 2000) is used in a preferred variant. The amount of mPEG 2000 with respect to the polymer is preferably 1:2-6, values close to a 1:4 ratio provide good results, for example, about 0.25 mg mPEG 2000/mg polymer. In this case the amount associated to the nanoparticles is 35.5 micrograms per mg nanoparticle. These nanoparticles are characterized by having a spherical shape and a size close to 300 nm.

In another variant of the invention the polyethylene glycol used has terminal functional groups different from the hydroxyl group, such as amino groups. These amino groups can in turn be substituted and have functional groups. In a preferred variant the amino groups are —$NH_2$. It has been observed that with these groups, the oral administration of the nanoparticles accumulate on certain segments of the intestinal tract, which allows a specific administration.

Therefore, in one variant the polyethylene glycol used in manufacturing pegylated nanoparticles is O,O-bis-(2-aminoethyl)polyethylene glycol 2000 (DAE-PEG 2000). In this case it is though that the structure of the pegylated nanoparticle is not the "brush" type structure because the chains would be joined at the two ends, giving rise to a "loop" type shape. The amount of DAE-PEG with respect to the polymer is preferably less than 1:4. In a preferred variant it is equal to or less than 0.25 mg DAE-PEG 2000/mg polymer. In this case the amount associated to the nanoparticles is about 90.6 micrograms per mg nanoparticle. These nanoparticles are characterized by having a spherical shape and a size close to 500 nm.

In another variant the polyethylene glycol used in preparing the pegylated nanoparticles has amino groups and branches in the alkyl group. It has been found that with these substituents the trend is to form a brush-type structure, with one of the ends inside the nanoparticle and the other one on the outside.

Therefore if the polyethylene glycol used is O,O'-bis-(2-aminopropyl)polypropylene glycol-polyethylene glycol-polypropylene glycol 2000 (DAP-PEG 2000) the nanoparticles are characterized by having a spherical shape and a size close to 360 nm. In this case the amount of DAP-PEG with respect to the polymer is preferably equal to or less than 0.25 mg DAP-PEG 2000/mg polymer), the amount associated to the nanoparticles is 67.6 micrograms per mg nanoparticle.

The chemical structures of some of polyalkylene glycols corresponding to the previously mentioned groups with different types of functional groups are illustratively provided below:
a) $H(OCH_2CH_2)_nOH$
b) $H_3C(OCH_2CH_2)_nOH$
c) $H_2N(CH_2CH_2O)_nCH_2CH_2NH_2$
d) $H_2NCHCH3CH_2(OCHCH3CH_2)(OCH_2CH_2)_n(OCH_2CHCH3)NH_2$ Specific examples would be:
a) polyethylene glycol 400, 1000 or 2000 (PEG 400, PEG 1000 or PEG 2000);
b) polyethylene glycol methyl ether 2000 (mPEG 2000);
c) O,O'-Bis-(2-aminoethyl)polyethylene glycol 2000 (DAE-PEG 2000);
d) O,O'-Bis-(2-aminopropyl)polypropylene glycol-polyethylene glycol-polypropylene glycol (DAP-PEG 2000);

As can be seen from the foregoing, which is confirmed by the examples, the selection of the type of polyethylene glycol allows modulating at will the features of the system which is generated. The use of mixtures of different types of polyethylene glycols adds an additional variability factor. From the practical point of view, this is important for adapting and selecting the most suitable system for each active molecule and for each administration method.

The process of preparing the biodegradable polymer and polyethylene glycol nanoparticles, preferably vinyl methyl ether and maleic anhydride (PVM/MA) copolymer and polyethylene glycol, is based on the solvent displacement method described in WO 02/069 938 for example.

In one variant of the invention, the pegylated nanoparticles are prepared by two different processes: (i) simultaneous incubation of the two polymers (for example PVM/MA and PEG) in the organic phase and (ii) incubation of the biodegradable polymer nanoparticles with an aqueous solution of polyethylene glycol. These processes are valid for preparing PVM/MA nanoparticles with the PEG association on their surface. The first variant (simultaneous incubation of polymers) is preferred because it provides a good degree of association of the PEG.

The first process includes simultaneously dissolving the biodegradable polymer and the polyethylene glycol in an organic solvent, such as acetone for example. The incubation of the mixture is carried out under stirring at room temperature for a certain time period. The concentration of the biodegradable polymer is preferably comprised between 0.001 and 10% w/v and the concentration of the polyethylene glycol or a derivative thereof between 0.001 and 5% w/v.

A certain volume of a polar solvent miscible with the solution of the polymers, such as ethanol for example, is optionally added to this solution.

A cross-linking agent can also optionally be used to improve the stability of the nanoparticles, as described in WO 02/069938. Among the cross-linking agents that can be used are diaminated molecules (for example 1,3 diaminopropane), polysaccharides or single saccharides, proteins, and generally any molecule having functional groups that are able to react with the Gantrez anhydride groups. In the process of the invention, cross-linking is not necessary when the PEGs are added because this occurs simultaneously. A very small amount of the indicated products must be added if cross-linking them is desired.

Finally a similar volume of a second non-solvent liquid is added, preferably a hydroalcoholic solution. In one variant pharmaceutical grade water is used (purified water of WFI, according to the application). The organic phase/hydroalcoholic solution ratio is preferably comprised in the range of 1/1-1/10. The nanoparticles are formed instantly in the medium with an appearance of a milky suspension.

The organic solvents are removed by any suitable process, such as evaporation under reduced pressure, the nanoparticles remaining in a stable aqueous suspension.

The nanoparticles are purified by conventional means, such as centrifugation, ultracentrifugation, tangential filtration or evaporation, including the use of a vacuum.

Finally, they can be lyophilized if desired for their long-term storage and preservation. Common cryoprotective agents such as sucrose or mannitol can be used to facilitate lyophilization preferably at a concentration comprised between 0.1 and 10% by weight.

The second process includes dissolving the biodegradable polymer in an organic solvent such as acetone. A certain volume of hydroalcoholic solution such as ethanol and finally a similar volume of water are subsequently added to this solution. The nanoparticles form instantly in the medium with an appearance of a milky suspension. The organic solvents are removed as described in the previous process, for example by evaporation under reduced pressure, the nanoparticles remaining in a stable aqueous suspension. Then the nanoparticles are incubated in an aqueous solution of polyethylene glycol. Incubation is carried out with stirring for a certain time period. The nanoparticles are subsequently purified by centrifugation and are finally lyophilized using the same processes described above.

The invention is also aimed at pharmaceutical compositions comprising the described pegylated nanoparticles and optionally an active molecule. Suitable pharmaceutical preparations are those known by a person skilled in the art for enteral formulations, preferably oral and parenteral formulations such as infusions, and topical formulations such as ophthalmic formulations. The formulations shall comprise the suitable excipients for each formulation. For example, in the case of oral formulations in tablet or capsule form, binders, disintegrating agents, lubricating agents, filler agents, enteric coating, etc., will be included if needed. The oral formulations are prepared conventionally by mixing, dry or wet granulation and incorporating the pegylated nanoparticles of the invention.

In one aspect of the invention the pegylated nanoparticles are administered by a route providing access to a mucosa of the organism (including oral, rectal, nasal, vaginal and ocular administration).

When the pegylated nanoparticles are administered parenterally, they are used to modify the distribution of the associated biologically active molecule and/or of the conventional nanoparticles. In the case of parenteral formulations, sterile suspensions or a lyophilizate of the nanoparticles and a reconstitution carrier, such as a physiological saline solution, are used. Excipients such as cryopreserving agents, pH regulating solutions and surfactants can be incorporated if needed.

The described pegylated nanoparticles and their formulations can be used as a basis for the administration of biologically active molecules. An active molecule is understood to be any chemical compound administered to a subject, preferably a human being, for prophylactic or therapeutic purposes. Of course the term also includes macromolecular compounds such as proteins, peptides, nucleic acids, etc. The pegylated nanoparticles are used to modify the distribution of the associated biologically active molecule.

In one variant the active molecule is from the group formed by DNA, RNA, nucleosides, nucleotides, oligonucleotides or polynucleotides. In another variant the active molecule is from the protein or peptide groups.

Active molecules from the groups formed by anti-tumor agents or antigenic agents for tumors, from the groups formed by protective agents of the central nervous system or glucocorticoids, etc., can be incorporated. Alternatively, the active molecule is an antigen for vaccination or an allergen for immunotherapy.

In one variant of the invention the pegylated nanoparticles can also be used as vaccine adjuvants.

The incorporation of the drug to the nanoparticles of the invention can be done as described in WO 02/069938, by incorporation to the polymer solution before nanoparticle formation, or by subsequently adding it to the aqueous suspension of the already formed nanoparticles. For example, and depending on the nature of the drug, the following process can be used:

a) Hydrophobic drugs: addition to the organic phase (acetone) and joint incubation/solubilization with PVMMA and PEG for a variable time period (up to 1 hour) with stirring (mechanical, magnetic or ultrasonic stirring).

b) Hydrophilic drugs: addition to the organic phase (acetone) and joint incubation with PVMMA and PEG for a variable time period (up to 1 hour) with stirring (mechanical, magnetic or ultrasonic stirring) until obtaining a thin acetone suspension. This process has been successfully used to encapsulate a protein model (ovalbumin, protein of about 44 kDa). The incorporation was efficient, allowing elevated encapsulation of the protein model.

c) Hydrophilic drugs: Addition in the aqueous phase to incubate with the pre-formed nanoparticles (this is the case used to encapsulate two fluorescent markers used in the examples: FITC and RBITC).

The invention is described below by means of several non-limiting and illustrative examples of the invention.

EXAMPLES

Several techniques have been used for the physicochemical characterization of the new nanoparticles. The size and zeta potential of the nanoparticles are determined in a Zetamaster apparatus (Malvern, United Kingdom). The shape of the nanoparticles can be observed by electron transmission microscopy (Zeiss, Germany) after marking the samples with phosphotungstic acid.

Example 1

Preparing Pegylated Nanoparticles with Polyethylene Glycol 2000 (PEG-NP)

Two processes have been tested:
mixing the two polymers in the organic phase
coating the pre-formed nanoparticles with PEG The yields of the process for manufacturing the pegylated nanoparticles are obtained by means of determining their weight at the end of the process and after their lyophilization. The manufacturing yields are expressed in percentages, calculated with respect to the initial mass of the PVM/MA-copolymer and of polyethylene glycol. The amount of polyethylene glycol associated to the nanoparticles is determined by colorimetry (Labsystems iEMS Reader MF), and is calculated as a difference between the initial amount used and the amount found in the supernatants obtained during the preparation of nanoparticles.

1.1. Association of Polyethylene Glycol to Vinyl Methyl Ether and Maleic Anhydride Copolymer in the Organic Phase This process is carried out by simultaneous incubation of PVM/MA and PEG 2000 in the organic phase.

To that end, 100 mg of PVM/MA are dissolved in 5 ml of organic solvent (acetone). Then PEG 2000 is added to this solution (10-50 mg). The mixture is left to react with magnetic stirring for 1 hour. Then 10 ml of ethanol and 10 ml of distilled water are added to this phase. The resulting mixture is left to homogenize for 5 minutes. The organic solvents are removed by evaporation under reduced pressure (Buchi R-144, Switzerland), concentrating the suspension of nanoparticles formed. The suspension is subjected to purification by centrifugation (20 minutes at 17000 rpm, twice) (Sigma 3K30, Germany). The supernatants are collected for analytical assessments whereas the residue is resuspended in a sucrose aqueous solution (5% w/v). The nanoparticle suspension is finally frozen and lyophilized in a Genesis 12EL apparatus (Virtis, USA).

The obtained nanoparticles have a spherical shape similar to conventional nanoparticles (FIG. 1 b). The properties of these pegylated nanoparticles are included in Table 1. The association of PEG 2000 to the nanoparticles causes an increase in the polydispersion of the population. It was observed that with an increase in the amount of polyethylene glycol (1:2 ratio), the size and especially the polydispersion become very high. The observations of surface potential of the nanoparticles show lower negative values for the pegylated nanoparticles. These results suggest the presence of the polyethylene glycol chains in the surface of the nanoparticles. It must finally be indicated that with PEG 2000: PVM/MA ratios of less than 1:4 w/w, the amount of PEG associated to the nanoparticles is maintained constant and close to 50 µg/mg.

TABLE 1

Influence of the amount of PEG 2000 on the physicochemical characteristics of the nanoparticles.

| PEG 2000 (mg) | Size (nm) | Polydispersion | Zeta potential (mV) | Amount of PEG 2000 (µg/mg)* |
|---|---|---|---|---|
| 0 | 289 ± 11 | 0.101 | −33.5 ± 6.6 | — |
| 10 | 317 ± 5 | 0.218 | −7.8 ± 0.5 | 44.9 ± 15.8 |
| 25 | 299 ± 22 | 0.210 | −14.6 ± 0.3 | 55.0 ± 12.0 |
| 50 | 400 ± 35 | 0.570 | −16.3 ± 10.0 | 128.2 ± 86.6 |

*Amount of PEG 2000 associated to the nanoparticles (expressed as µg PEG/mg nanoparticles) according to the colorimetric method.
The data express the media ± S.D. (n = 3).

1.2. Association of Polyethylene Glycol to the Pre-Formed Nanoparticles 100 mg of PVM/MA are dissolved in 5 ml of organic solvent (acetone). Then 10 ml of ethanol and 10 ml of distilled water are added to this solution with stirring. The resulting mixture is left to homogenize for 5 minutes. Then the nanoparticle suspension is evaporated under reduced pressure until both solvents are eliminated. The aqueous nanosuspension volume is adjusted with water to 5 ml and 5 ml of an aqueous solution containing between 10-25 mg of PEG 2000 are added. The incubation of the nanoparticles in the polyethylene glycol phase is carried out with magnetic stirring for 1 hour. The suspension is subjected to purification by centrifugation (20 minutes at 17000 rpm, twice) (Sigma 3K30, Germany). The supernatants are removed and the residue is resuspended in a sucrose aqueous solution (5% w/v). The nanoparticle suspension is finally frozen and lyophilized in a Genesis 12EL apparatus (Virtis, USA).

Figure 2:
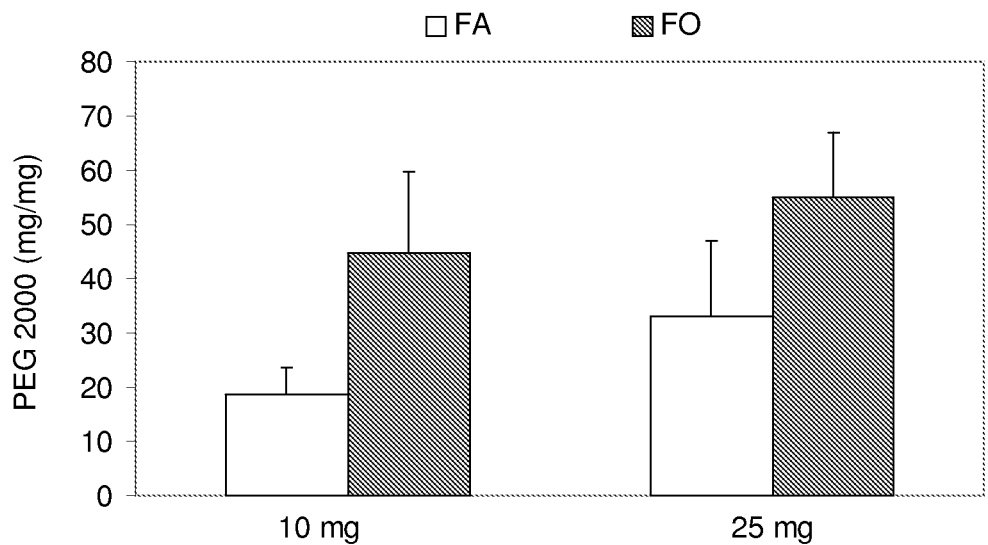
FIG. 2 shows the association of PEG 2000 (mg/mg) according to the process used: simultaneous incubation of PEG and PVM/MA in the organic phase (OP) or incubation of nanoparticles with the aqueous solution (AP) of the PEG.

The amount of polyethylene glycol associated to the nanoparticles is determined by the previously indicated colorimetric method. The results show that by this process, the amount of PEG associated to the nanoparticles is considerably lower than by the process described in Example 1.1 (incubation in the organic phase) (FIG. 2). The reason for this result is the high affinity of polyethylene glycol for water, therefore an effective association with the carboxylic groups coming from the hydrolysis of the copolymer in the pre-formed particles is not obtained. It can be concluded that the method of obtaining pegylated nanoparticles by simultaneous incubation of the copolymer and polyethylene glycol in an organic phase is more efficient than the simple coating of the pre-formed nanoparticles with PEG.

1.3. Influence of the Molecular Weight of PEG on the Physicochemical Characteristics of Pegylated Nanoparticles The process is carried out by simultaneous incubation of PVM/MA and the desired polyethylene glycol (PEG 400, PEG 1000 or PEG 2000) as described in Example 1.1.

To that end, 100 mg of PVM/MA are dissolved in 5 ml of organic solvent (acetone). Then 25 mg of PEG (400, 1000 or 2000) are added. The mixture is left to react with magnetic stirring for 1 hour. Then 10 ml of ethanol and 10 ml of distilled water are added to this phase. The resulting mixture is left to homogenize for 5 minutes. The organic solvents are removed by evaporation under reduced pressure (Buchi R-144, Switzerland), concentrating the nanoparticle suspension. The suspension is subjected to purification by centrifugation (20 minutes at 17000 rpm, twice) (Sigma 3K30, Germany). The supernatants are removed and the residue is resuspended in a sucrose aqueous solution (5% w/v). The nanoparticle suspension is finally frozen and lyophilized in a Genesis 12EL apparatus (Virtis, USA).

The amounts of PEG (400, 1000 or 2000) and mPEG 2000 (Example 2) are determined by calorimetric assessment. To that end, 15 µl of an iodine solution (10 mg/ml of iodine; 20 mg/ml of potassium iodide) are added to 1 ml of the supernatants obtained during the nanoparticle purification step. The absorbance of the complex obtained between PEG (or mPEG) and iodine is observed by colorimetry at λ 540 nm (Sims & Snape, Anal. Biochem., 107 (1980) 60-63).

Table 2 shows the influence of the molecular weight of PEG on the physicochemical characteristics of the obtained nanoparticles. Due to these results, it can be concluded that low molecular weight polyethylene glycols are not suitable for pegylation of these nanoparticles. In the case of PEG 400, which is liquid, association cannot be obtained, and in the case of PEG 1000, the association is very low. These results are also confirmed from the study of the surface charge of the particles. The zeta potential of the nanoparticles modified with PEG 400 or PEG 1000 is always more negative than that of the particles pegylated with PEG 2000, and is similar to that of the non-coated particles. It can be concluded that pegylation with PEG 2000 is much more efficient.

TABLE 2

Influence of the molecular weight of PEG on the physicochemical characteristics of the pegylated nanoparticles (PEG/PVM-MA ratio = 0.25).

| Type of nanoparticles | Amount µg PEG/mg nanoparticles | | Size (nm) | Zeta potential (mV) |
|---|---|---|---|---|
| | Colorimetry | $^1$H - NMR | | |
| NP* | — | — | 289 ± 11 | −33.5 ± 6.6 |
| PEG 400 - NP | ND** | ND** | 241 ± 6 | −40.1 ± 1.5 |
| PEG 1000 - NP | ND** | 19.8 | 271 ± 10 | −45.3 ± 5.0 |
| PEG 2000 - NP | 55.0 ± 12.0 | 30.2 | 299 ± 22 | −14.6 ± 0.3 |

*NP - nanoparticles not treated with PEG
**ND—not detectable
[1]Determination of the amount of PEG associated to the nanoparticles by nuclear magnetic resonance (method described in Example 5).
The data express the mean ± S.D. (n = 3).

Example 2

Preparing Pegylated Nanoparticles with Polyethylene Glycol Methyl Ether 2000 (mPEG-NP)

This process is carried out by simultaneous incubation of PVM/MA and mPEG in an organic phase.

To that end, 100 mg of the copolymer PVM/MA are dissolved in 5 ml of organic solvent (acetone). Then, an amount of mPEG 2000 is added to this solution (10-50 mg). The mixture is left to react with magnetic stirring for 1 hour. Then, 10 ml of ethanol and 10 ml of distilled water are added to this phase. The resulting mixture is left to homogenize for 5 minutes. The organic solvents are removed by evaporation under reduced pressure (Buchi R-144, Switzerland), concentrating the nanoparticle suspension. The suspension is subjected to purification by centrifugation (20 minutes at 17000 rpm, twice) (Sigma 3K30, Germany). The supernatants are removed and the residue is resuspended in a sucrose aqueous solution (5% w/v). The nanoparticle suspension is finally frozen and lyophilized in a Genesis 12EL apparatus (Virtis, USA).

FIG. 1(c) shows that the nanoparticles coated with mPEG 2000 have a spherical shape and the surface seems to be smooth. Table 3 shows the level of association of mPEG 2000 to the nanoparticles and their influence on size, polydispersion and surface charge of the nanoparticles. The results show that with an increase in the initial amount of mPEG 2000, the percentage associated to the nanoparticles slightly increases.

The presence of mPEG increases polydispersion of the nanoparticle population, especially at a high concentration (mPEG/PVM-MA ratio greater than 0.25). On the other hand, the negative charge of the nanoparticles decreases when the amount of mPEG used increases. However, the considerable deviations observed when high amounts of mPEG are used suggest that the surface distribution of the mPEG 2000 chains is not homogenous.

TABLE 3

Influence of the amount of mPEG 2000 on the physicochemical characteristics of the nanoparticles.

| mPEG 2000 (mg) | Size (nm) | Polydispersion | Zeta potential (mV) | Amount mPEG 2000 (μg/mg)* |
|---|---|---|---|---|
| 0 | 289 ± 11 | 0.101 | −33.5 ± 6.6 | — |
| 10 | 254 ± 9 | 0.128 | −19.7 ± 7.4 | 36.1 ± 14.3 |
| 25 | 272 ± 17 | 0.151 | −11.8 ± 2.2 | 35.5 ± 7.5 |
| 50 | 329 ± 20 | 0.350 | −21.0 ± 10.0 | 116.8 ± 68.4 |

*Amount of mPEG 2000 associated to the nanoparticles (expressed as μg mPEG/mg nanoparticles) according to the colorimetric method.
The data express the mean ± S.D. (n = 3).

Example 3

Preparing Pegylated Nanoparticles with O,O'-Bis-(2-Aminoethyl) Polyethylene Glycol 2000 (DAE-PEG-NP)

This process is carried out by simultaneous incubation of PVM/MA and DAE-PEG 2000 in an organic phase.

To that end, a certain amount of DAE-PEG (5, 10, 25 or 35 mg) is dissolved in 5 ml of organic solvent (acetone). Then 100 mg of PVM/MA are added to this solution with magnetic stirring. The resulting mixture is left to react with magnetic stirring for 1 hour. 10 ml of ethanol and 10 ml of distilled water are added to this organic phase with stirring. The resulting mixture is left to homogenize for 5 minutes. The organic solvents are removed by evaporation under reduced pressure (Buchi R-144, Switzerland), concentrating the nanoparticle suspension. The suspension is subjected to purification by centrifugation (20 minutes at 17000 rpm, twice) (Sigma 3K30, Germany). The supernatants are removed and the residue is resuspended in a sucrose aqueous solution (5% w/v). The nanoparticle suspension is finally frozen and lyophilized in a Genesis 12EL apparatus (Virtis, USA).

The amount of DAE-PEG and of DAP-PEG (example 4) is determined after adding the reagent Micro BCA™ Protein Assay Reagent Kit (Pierce, U.S.A.) to the supernatants obtained for the nanoparticle purification step. This reagent is able to interact with the amino groups of these polyethylene glycols giving a colored complex. To that end, 150 μl of reagent are added to the same volume of supernatant. Absorbance is determined by colorimetry at λ 570 nm after incubation for two hours at 37° C.

FIG. 1 (d) shows that the nanoparticles coated with DAE-PEG 2000 have a spherical shape. The Table 4 shows the level of the association of DAE-PEG 2000 and its influence on size, polydispersion and surface charge of the nanoparticles. The results show that increasing the amount of DAE-PEG 2000 (from 5 to 35 mg) increases the amount of excipient attached to the nanoparticles. However, when the amount of DAE-PEG 2000 used is greater than 25 mg, the nanoparticles are not formed.

When analyzing the size, it is observed how increasing the degree of association produces nanoparticles with a larger size and greater polydispersion. Therefore, when the DAE-PEG nanoparticles are produced with 25 mg, the resulting particles have a size greater than 500 nm and very high polydispersion. On the other hand, a reduction in the negative surface charge of the coated nanoparticles in comparison with the non-coated nanoparticles is observed. These data suggest that the DAE-PEG 2000 chains are present in the surface of the nanoparticles.

TABLE 4

Influence of the amount of DAE-PEG on the physicochemical characteristics of the nanoparticles.

| DAE-PEG (mg) | Size (nm) | Polydispersion | Zeta potential (mV) | Amount DAE-PEG (μg/mg)* |
|---|---|---|---|---|
| 0 | 289 ± 11 | 0.101 | −33.5 ± 6.6 | — |
| 5 | 324 ± 14 | 0.207 | −14.0 ± 9.0 | 27.0 ± 7.0 |
| 10 | 387 ± 23 | 0.296 | −11.9 ± 3.5 | 71.1 ± 24.0 |
| 25 | 505 ± 88 | 0.946 | −5.5 ± 1.5 | 90.6 ± 6.0 |

*Amount of DAE-PEG 2000 associated to the nanoparticles (expressed as μg DAE-PEG/mg nanoparticles) according to the colorimetric method.
The data express the mean ± S.D. (n = 3).

Example 4

Preparing Pegylated Nanoparticles with O,O'-Bis-(2-Aminopropyl)-Polypropylene Glycol-Polyethylene Glycol-Polypropylene Glycol 2000 (DAP-PEG-NP)

This process is carried out by simultaneous incubation of PVM/MA and DAP-PEG 2000 in an organic phase.

To that end, a certain amount of DAP-PEG 2000 (10-50 mg) is dissolved in 5 ml of organic solvent (acetone). Then 100 mg of the vinyl methyl ether and maleic anhydride copolymer are added to this solution with magnetic stirring. The resulting mixture is left to react with magnetic stirring for 1 hour. Then 10 ml of ethanol and 10 ml of distilled water are added to this phase with stirring. The resulting mixture is left to homogenize for 5 minutes. The organic solvents are removed by evaporation under reduced pressure (Buchi R-144, Switzerland), concentrating the nanoparticle suspension. The suspension is subjected to purification by centrifugation (20 minutes at 17000 rpm, twice) (Sigma 3K30, Germany). The supernatants are removed and the residue is resuspended in a sucrose aqueous solution (5% w/v). The nanoparticle suspension is finally frozen and lyophilized in a Genesis 12EL apparatus (Virtis, USA)

FIG. 1 (e) shows that the nanoparticles coated with DAP-PEG 2000 have a spherical shape and a smooth surface. Table 5 shows the general characteristics of these nanoparticles. The results show that increasing the amount of DAP-PEG 2000 increases its amount attached to the nanoparticles. However, when the amount of DAP-PEG 2000 used is greater than 35 mg, the nanoparticles are not formed.

It is observed that increasing the degree of association produces nanoparticles with a larger size and also greater polydispersion. The observations of the zeta potential show a significant reduction of the negative values obtained for the coated nanoparticles (values close to zero). These results suggest that the DAP-PEG 2000 chains are preferably located in the surface of the nanoparticles.

TABLE 5

Influence of the amount of DAP-PEG 2000 in the physicochemical characteristics of the nanoparticles.

| DAP-PEG (mg) | Size (nm) | Polydispersion | Zeta potential (mV) | Amount DAP-PEG (µg/mg)* |
|---|---|---|---|---|
| 0 | 289 ± 11 | 0.101 | −33.5 ± 6.6 | — |
| 10 | 347 ± 7 | 0.089 | −4.1 ± 1.7 | ND** |
| 25 | 361 ± 15 | 0.169 | −2.7 ± 0.8 | 67.6 ± 17.6 |
| 35 | 512 ± 12 | 0.372 | −6.9 ± 0.7 | 101.1 ± 11.9 |

*Amount of DAP-PEG 2000 associated to the nanoparticles (expressed as µg DAP-PEG/mg nanoparticles) according to the colorimetric method.
**ND—not detectable
The data express the mean ± S.D. (n = 3).

Example 5

Figure 3:
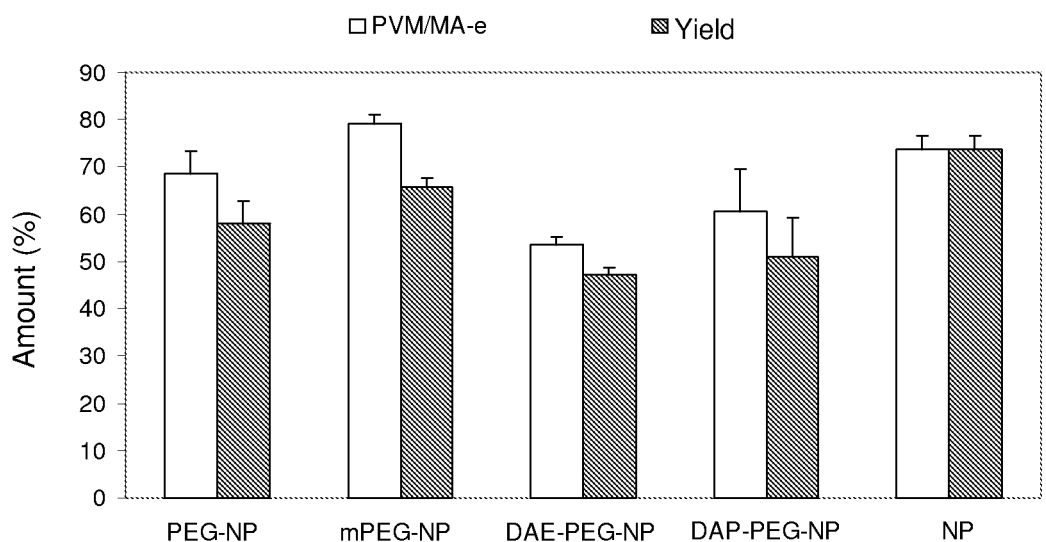
FIG. 3 shows the effect of the type of polyethylene glycol on the percentage of PVM/MA converted into nanoparticles (PVM/MA-e) and on the process yield.

Study of the Yield of the Process and of the Structure of the Pegylated Nanoparticles FIG. 3 shows the influence of the type of polyethylene glycol in the percentage of PVM/MA transformed into nanoparticles, and in the total yield of the process. In general the percentage of copolymer transformed into nanoparticles is close to 73%. It is observed that when the nanoparticles are modified with PEG or mPEG, the percentage of PVM/MA transformed into particles is not significantly modified. However, nanoparticle pegylation with DAE-PEG or DAP-PEG decreases the process yield.

The association of polyethylene glycols to the nanoparticles is confirmed by the element analysis method (Leco CHN-900, U.S.A.). According to this technique, they may show changes in their oxygen, hydrogen or nitrogen composition when associated to other components (for example: PEG).

Table 6 includes the C, H, O and N element composition of the different types of pegylated nanoparticles. Compared with conventional nanoparticles (NP), all the pegylated nanoparticles show an increase in the percentage of hydrogen (H) and a relative decrease in their oxygen content. On the other hand, DAE-PEG NP and DAP-PEG NP show the presence of nitrogen which is not observed in the non-modified nanoparticles.

TABLE 6

Comparison between the element percentages of pegylated nanoparticles and non-modified particles (NP).

| | Percentage (%) | | | |
|---|---|---|---|---|
| Sample | C | H | O | N |
| NP | 51.72 | 5.24 | 43.04 | — |
| PEG - NP | 51.39 | 5.44 | 43.17 | — |
| mPEG - NP | 52.00 | 5.47 | 42.53 | — |
| DAE-PEG - NP | 51.24 | 5.92 | 42.69 | 0.14 |
| DAP-PEG - NP | 52.78 | 5.79 | 41.10 | 0.33 |

Figure 4:
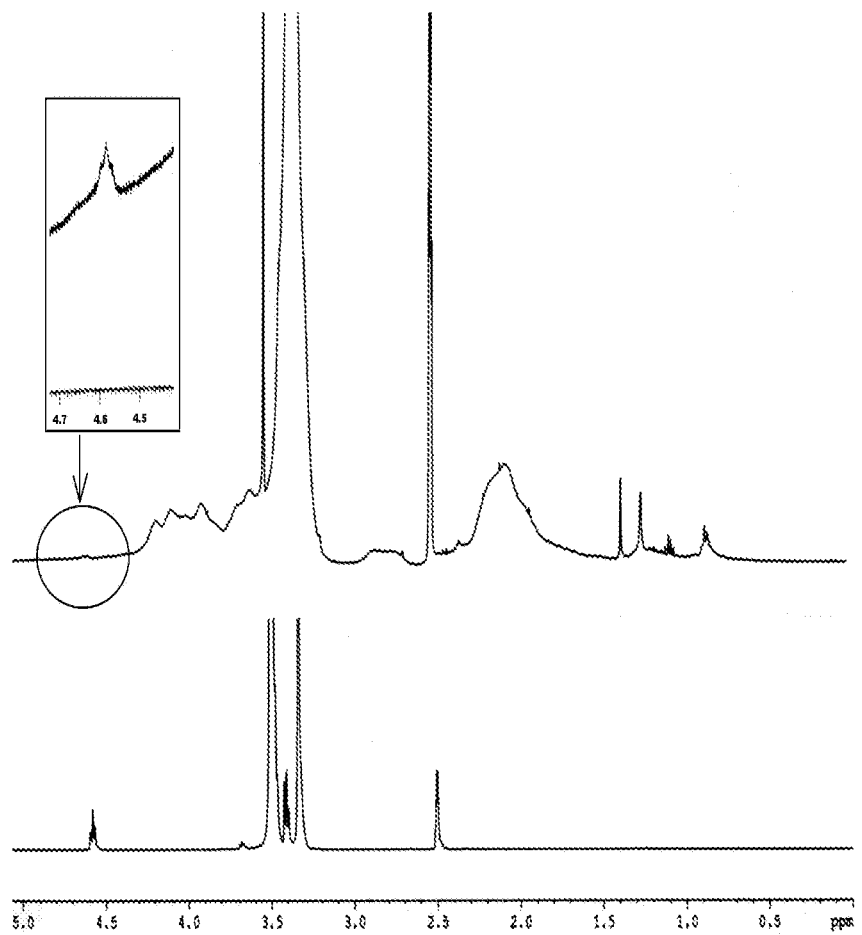
FIG. 4 shows nuclear magnetic resonance spectrums of the pegylated nanoparticles with PEG 2000 (top) and of free PEG 2000 (bottom). The amplified image of the peak at 4.58 ppm (protons of the hydroxyl group) is shown in the box.

The location or the polyethylene glycols (inside or in the surface of the nanoparticles) is analyzed by nuclear magnetic resonance ($^1$H-NMR) (Bruker 400 Ultrashield™, Germany) after dissolving 5 mg of pegylated nanoparticles in 0.5 ml of deuterated dimethyl sulfoxide. The spectrums of pegylated nanoparticles with PEG and mPEG are obtained after applying 6400 sweeps, whereas the spectrums of DAE-PEG-NP and DAP-PEG-NP after 12800 sweeps. The spectrums show the typical hydrogen peak of the polyethylene units (at 3.51 ppm, —OCH$_2$CH$_2$—) and the hydrogen peaks of the hydroxyl groups (in the case of PEG and mPEG), or the hydrogen peaks of the amino groups of DAE-PEG and of DAP-PEG (at 4.58 ppm) (FIG. 4). A ratio of the values of areas of these two peaks is in the spectrums of the pegylated particles and in the spectrums of the free polyethylene glycols is calculated. The values of these ratios can provide information for locating the polyethylene glycol chains in the pegylated nanoparticles.

Figure 5:
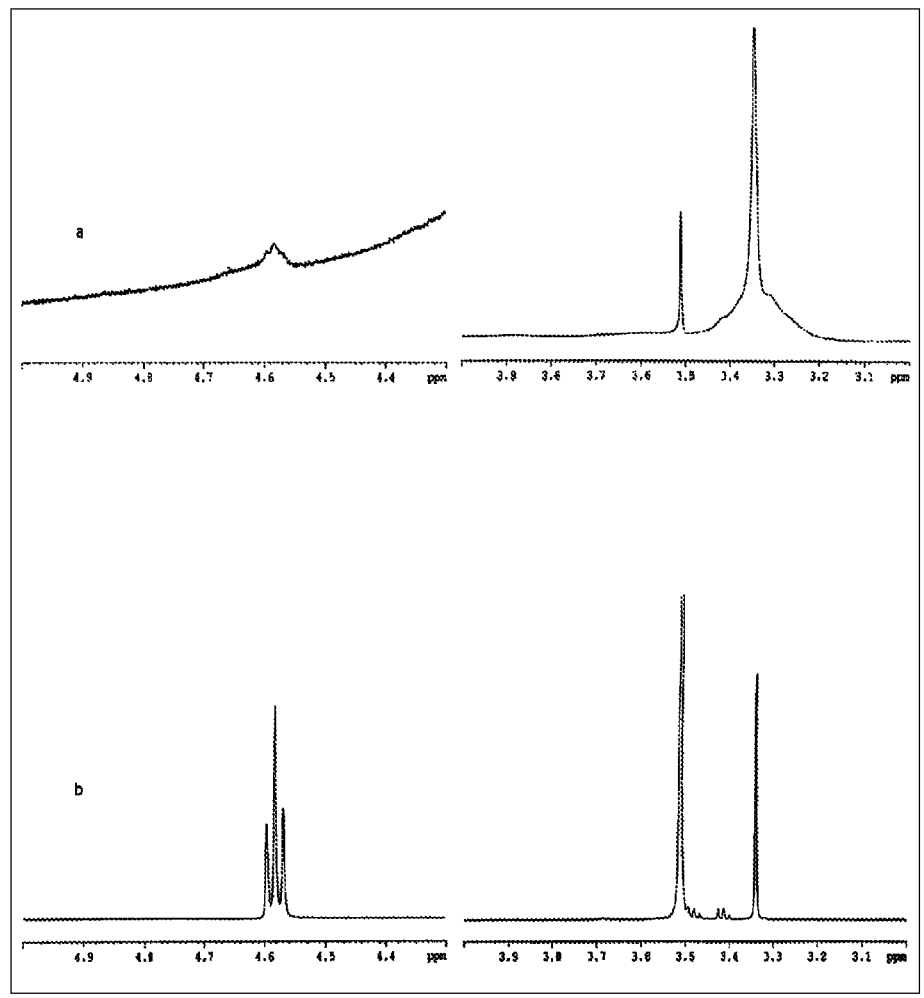
FIG. 5 shows details of the nuclear magnetic resonance spectrums (a) of the pegylated nanoparticles with PEG 2000 and (b) of free PEG 2000, dissolved in DMSO (5 mg in 0.5 ml).

It is observed that the hydrogen peak of the hydroxyl group (4.58 ppm) appears in the spectrum of the pegylated nanoparticles with PEG 2000 (FIG. 5 a). Table 7 shows the area of the two previously mentioned peaks (at 3.51 ppm and at 4.58 ppm) and the ratios between them for PEG-NP and free PEG. It is calculated that the ratio between these two peaks for nanoparticles is about two times greater than for free PEG 2000. In the case of these nanoparticles these data mean that the proportion of hydroxyl groups is two times less, therefore it can be concluded that a significant number of these functional groups (which do not appear in the spectrum) are attached to the anhydride groups of the copolymer. According to these observations, a small part of the PEG 2000 chains would be included inside the nanoparticles, whereas most of the PEG chains would be arranged in the surface thereof. This fact corroborates the zeta potential data shown in Table 1.

Table 7 shows the data referring to the areas of the two peaks for m-PEG-NP and free mPEG 2000. It is observed that the ratio between the two peaks for the pegylated nanoparticles and mPEG 2000 is similar (177 vs. 217). These results show that the mPEG hydroxyl group proportion in the two cases (nanoparticles and free mPEG) is similar and that a small percentage reacts with the anhydride groups of the copolymer. It can be concluded that the structure of these particles is different from that of PEG-NP. In this case, a greater percentage of mPEG chains would be included inside, and only a small part thereof would be located in the surface of the nanoparticles. Therefore the surface distribution of the mPEG chains is not homogenous, which is consistent with the large deviations observed in the analysis of the zeta potential of these particles (Table 3).

TABLE 7

Analysis of the spectrums of PEG 2000 and pegylated nanoparticles with PEG 2000 by means of the nuclear magnetic resonance (H-NMR) method.

| | Area of the peaks | | |
|---|---|---|---|
| Shows | Peak A 3.51 ppm (hydrogen of the polyethylene units) | Peak B 4.58 ppm (hydroxyl hydrogen) | Ratio A/B |
| PEG 2000 | $75.35 \times 10^9$ | $73.65 \times 10^7$ | 102.5 |
| PEG - NP | $2.03 \times 10^9$ | $1.11 \times 10^7$ | 183.3 |
| mPEG | $46.00 \times 10^9$ | $26.01 \times 10^7$ | 176.8 |
| mPEG - NP | $2.30 \times 10^9$ | $1.06 \times 10^7$ | 217.0 |

Figure 6:
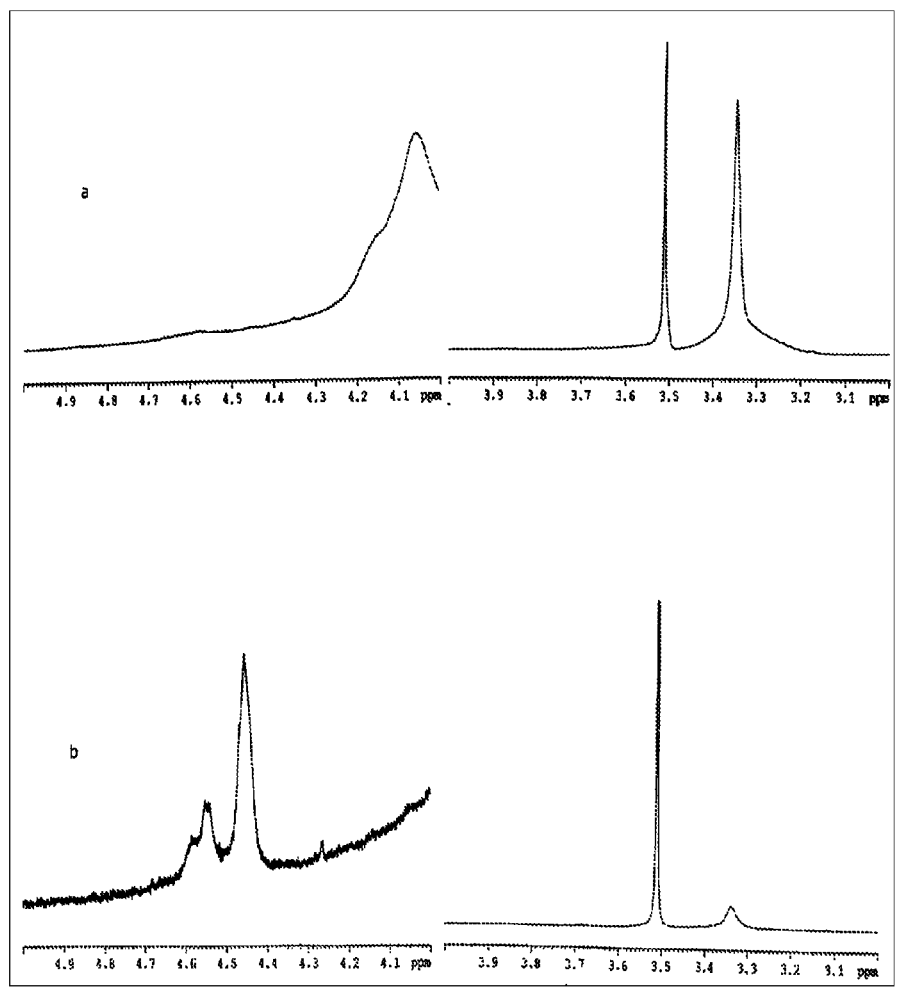
FIG. 6 shows details of the nuclear magnetic resonance spectrums (a) of the pegylated nanoparticles with DAP-PEG 2000 and (b) of free DAP-PEG 2000, dissolved in DMSO (5 mg in 0.5 ml).

Table 8 shows the data referring to the areas of the peaks for DAP-PEG-NP and free DAP-PEG 2000. In the DAP-PEG 2000 spectrum, there are two signals corresponding to hydrogens of the two different amino groups located at the ends of its chain: a doublet at δ=4.55 ppm and another one at δ=4.45 ppm (FIG. 6 b). It is observed that in the spectrum of the pegylated nanoparticles with DAP-PEG 2000, there is no hydrogen of these amino groups (FIG. 6 a), which indicates that all the amino groups of this type of polyethylene glycol react with the anhydride groups of the polymer forming the nanoparticles. Furthermore, the DAP-PEG chains would be attached to the surface of the nanoparticles at the two end amino groups and the surface coating would be complete. This would be supported by the zeta potential values (close to cero) of these particles (Table 5).

TABLE 8

Analysis of the spectrums of DAP-PEG 2000 and of the pegylated nanoparticles (DAP-PEG - NP) by means of the nuclear magnetic resonance (H-NMR) method.

| Shows | Area of the peaks | | |
|---|---|---|---|
| | Peak A 3.51 ppm (hydrogen of the polyethylene units) | Peak B 4.55 ppm (amino group hydrogen) | Peak C 4.45 ppm (amino group hydrogen) |
| DAP-PEG | $115.14 \times 10^9$ | $9.83 \times 10^6$ | $21.46 \times 10^6$ |
| DAP-PEG - NP | $9.81 \times 10^9$ | — | — |

Figure 7:
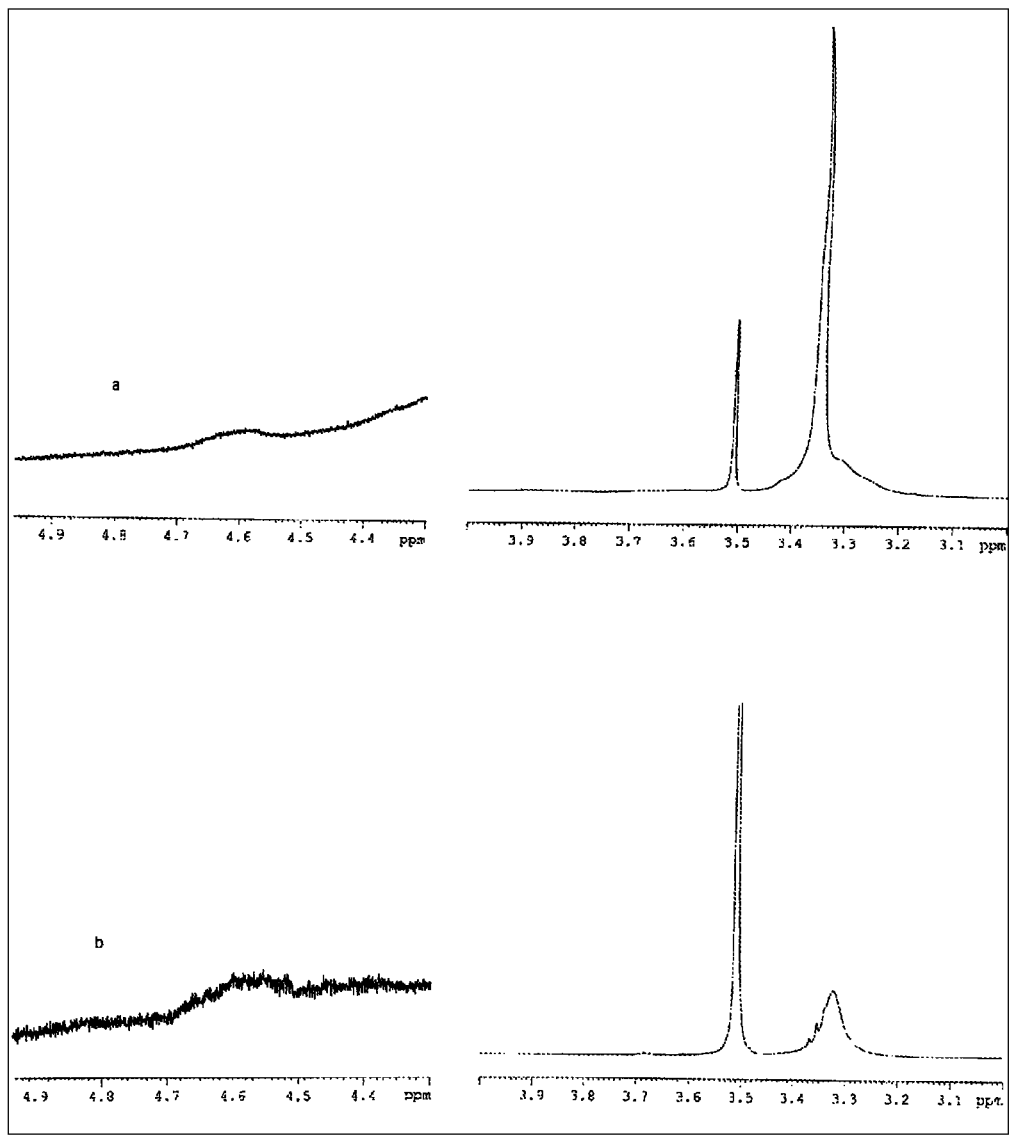
FIG. 7 shows details of the nuclear magnetic resonance spectrums (a) of the pegylated nanoparticles with DAE-PEG 2000 and (b) of free DAE-PEG 2000, dissolved in DMSO (5 mg in 0.5 ml).

In the case of DAE-PEG 2000, it is not possible to calculate the same ratio between the two peaks because the peak at 4.58 ppm has a very low intensity and low resolution (independent of the concentration and number of sweeps carried out) (FIG. 7 b). In any case, it can be observed that this peak appears in the spectrum of the nanoparticles as well as in the spectrum of DAE-PEG 2000. Therefore, it can be concluded that part of the DAE-PEG chains would be included inside the particles. However, most of them would be located in the surface attached only at the end of the chain of this polyethylene glycol.

Figure 8:
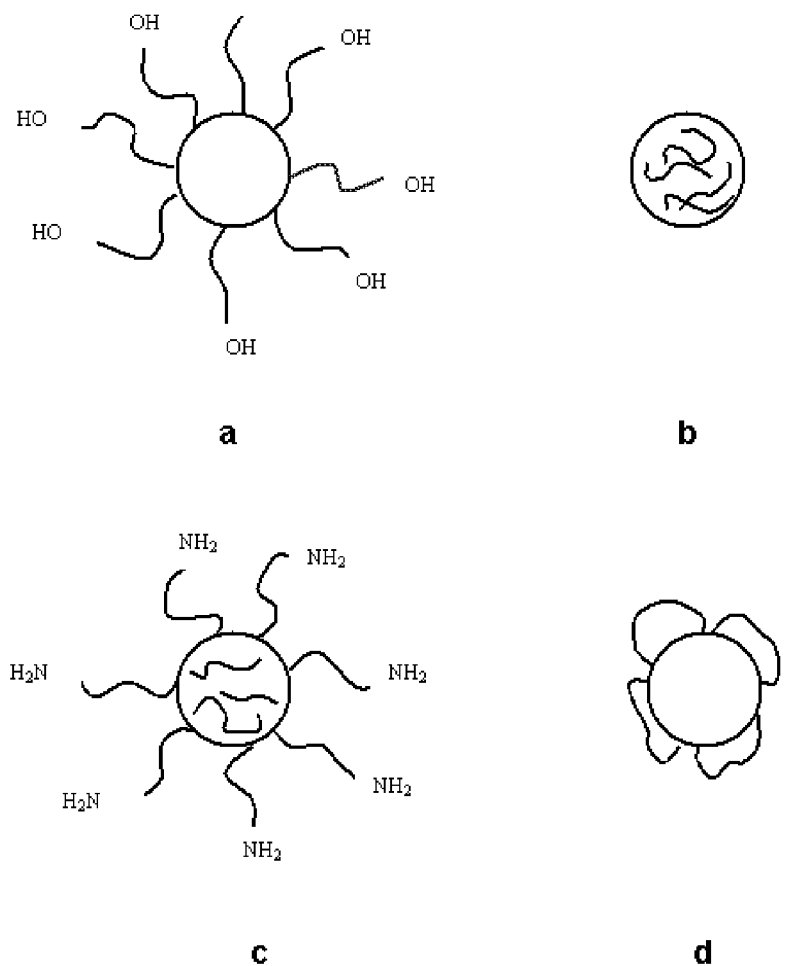
FIG. 8 shows structures proposed for the different pegylated nanoparticles from the nuclear magnetic resonance data and the zeta potential values—a) PEG-NP; b) mPEG-NP; c) DAE-PEG-NP; d) DAP-PEG-NP.

With respect to these data, it can be concluded that the pegylated nanoparticles have a different structure. The structure proposed for the different formulations is shown in FIG. 8. Certain polyethylene glycols such as PEG 2000, DAE-PEG and DAP-PEG, modify the surface of the developed nanoparticles. In the case of PEG-NP and DAE-PEG-NP, the coating would give rise to a "brush"-type structure (FIGS. 8 a and c), whereas in the case of DAP-PEG, the chains would be attached at the two ends giving rise to a "loop"-type formation (FIG. 8 d). The only case in which modification of the nanoparticle surface is not observed is when mPEG 2000 is used. mPEG would mostly be found inside the nanoparticles (FIG. 8 b).

Example 6

Study of the Bioadhesive Characteristics of Pegylated Nanoparticles in the Gastrointestinal Tract of Rats This study was carried out according to the regulations of the Ethics Committee of the University of Navarra in accordance with European laws on experimenting with animals (86/609/EU).

The pegylated nanoparticles used in this assay are fluorescently marked with rhodamine B isothiocyanate. To that end, the nanoparticles are formed by means of simultaneous incubation of PVM/MA and the different types of polyethylene glycols (according to the process in Examples 1.1, 2, 3 and 4). Then 10 ml of ethanol and 10 ml of distilled water are added to this phase with stirring. The resulting mixture is left to homogenize for 5 minutes. The organic solvents are removed by evaporation under reduced pressure (Buchi R-144, Switzerland), concentrating the nanoparticle suspension. The volume of aqueous nanosuspension is adjusted with water to 9 ml and 1 ml of a rhodamine B isothiocyanate aqueous solution (1.25 mg/ml) is added. The incubation of the nanoparticles with the fluorescent marker is carried out with stirring for 5 minutes. Then the fluorescently modified nanoparticle suspension is subjected to purification by centrifugation (20 minutes at 17000 rpm, twice) (Sigma 3K30, Germany). The supernatants are removed and the residue is resuspended in a sucrose aqueous solution (5% w/v). The nanoparticle suspension is finally frozen and lyophilized in a Genesis 12EL apparatus (Virtis, USA).

Table 9 includes the characteristics of the formulations used in this assay and fluorescently marked with rhodamine B isothiocyanate.

TABLE 9

Physicochemical characteristics of the nanoparticles considered in the bioadhesion study. Mean ± SD (n = 3).

| Samples | Size (nm) | Zeta potential (mV) | Polyethylene glycol (μg/mg)* | Rhodamine (μg/mg)** |
|---|---|---|---|---|
| NP | 289 ± 11 | −33.5 ± 6.6 | — | 10.33 ± 0.87 |
| PEG - NP | 299 ± 22 | −14.6 ± 0.3 | 55.0 ± 12.0 | 10.37 ± 0.09 |
| mPEG - NP | 272 ± 17 | −11.8 ± 2.2 | 35.5 ± 7.5 | 10.46 ± 0.11 |
| DAE-PEG - NP | 505 ± 88 | −5.5 ± 1.5 | 90.6 ± 6.0 | 10.04 ± 0.62 |
| DAP-PEG - NP | 361 ± 15 | −2.7 ± 0.8 | 67.6 ± 17.6 | 8.74 ± 0.75 |

*Amount of polyethylene glycol associated to the nanoparticles (μg PEG/mg nanoparticles).
**The amount of rhodamine B isothiocyanate attached to nanoparticles (expressed in μg/mg nanoparticles) is determined by colorimetry at 540 nm.

The obtained nanoparticles (10 mg) are orally administered to male rats (Wistar type, weight 220.0 g) after their dispersion in 1 ml of water. After the oral administration, the animals are sacrificed by cervical dislocation at different times: 0.5, 1, 3 and 8 hours. The abdominal cavity is opened and the gastrointestinal tract extracted. The area is divided into the following anatomical portions: stomach, small intestine and cecum. Each segment is longitudinally opened through the mesentery and is washed with saline phosphate buffer (pH=7.4; 0.15 M) to remove the non-adhered nanoparticle fraction. Furthermore, each segment is cut into portions of a length of 2 cm digested for 24 hours with 1 ml of 3M sodium hydroxide (Arbos et al., Int. J. Pharm., 242 (2002) 129-136). Then the rhodamine is removed with 2 ml of methanol and the samples are centrifuged for 10 minutes at 4000 rpm. The supernatants (1 ml) are diluted with 3 ml of water and the amount of rhodamine is determined by means of fluorescence spectroscopy at $\lambda_{ex}$=540 nm and $\lambda_{em}$=580 nm (GENios, Austria). The fraction of nanoparticles adhered to the mucosa can be estimated according to this process.

Figure 9:
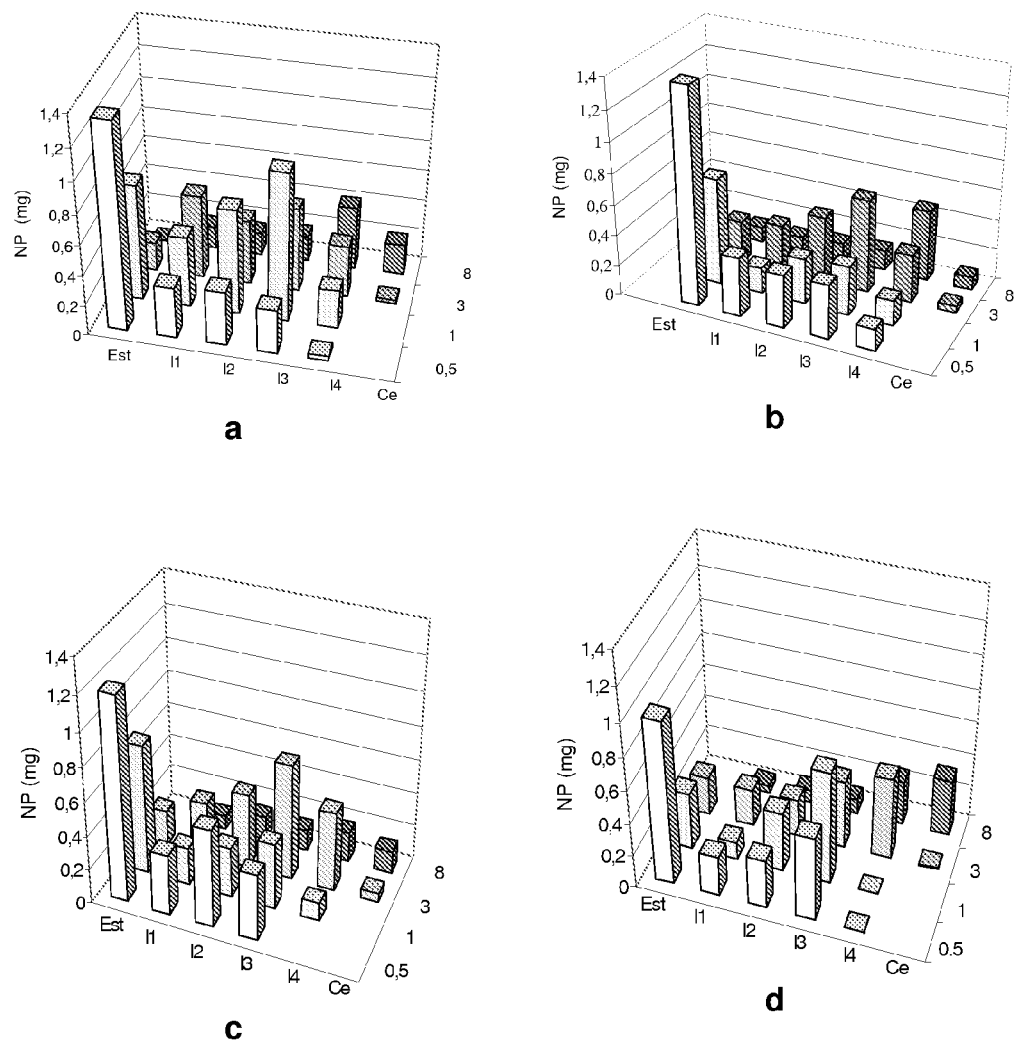
FIG. 9 shows the distribution of the pegylated nanoparticles in the gastrointestinal tract after their oral administration in rats: (a) PEG-NP, (b) mPEG-NP, (c) DAE-PEG-NP and (d) DAP-PEG-NP. The x-axis represents the amount of adhered nanoparticles (NP) (mg); the y-axis shows the different portions of the tract (St: stomach; I1, I2, I3, I4: intestinal portions; Ce: Cecum; the z-axis represents the time after the administration (hours).

The specific distribution of the pegylated nanoparticles in the different parts of the gastrointestinal tract is shown in FIG. 9. All the formulations showed a significant initial adhesion to the mucosa of the stomach. The percentage of the dose adhered to this organ 30 minutes after its administration ranged between 13% for PEG-NP and 9% for DAP-PEG-NP. All the pegylated nanoparticle formulations also showed a certain affinity for the $I_3$ portion of the small intestine; however, PEG-NP and DAE-PEG-NP were shown to be the most efficient formulations 3 hours after administration for maintaining amounts adhered to the small intestine, close to 20% of the dose. Finally, the peak of adhered nanoparticles 8 hours after the administration was found in the last portion of the small intestine (for PEG-NP) or in the cecum (for mPEG-NP and DAP-PEG-NP). A relatively significant fraction (close to 10%) of nanoparticles adhered to the mucosa could still be quantified in the case of PEG-NP and DAP-PEG-NP. In conclusion, it can be asserted that the nanoparticles coated with PEG 2000 and mPEG 2000 show a very homogenous distribution and are disseminated on all the parts of the tract for 8 hours (FIGS. 9 a and b). The pegylated nanoparticles with DAE-PEG are preferably adhered in the intermediate portions of the small intestine (FIG. 9 c), whereas the nanoparticles modified with DAP-PEG 2000 accumulate mainly in the distal regions of the intestinal tract (FIG. 9 d). These results mean that the nanoparticles herein developed can provide a specific drug release.

Bioadhesion parameters (Arbos et al., Int. J. Pharm., 242 (2002) 129-136): The adhesion curve of each formulation was obtained by representing the adhered fraction of pegylated nanoparticles in the gastrointestinal mucosa of rats over time. The following bioadhesion parameters were calculated from this curve: $AUC_{adh}$, $k_{adh}$ and $MRT_{adh}$. $k_{adh}$ represents the elimination rate of the adhered fraction and was calculated with the aid of the WinNonlin version 1.5 program (Scientific Consulting, Inc.). $AUC_{adh}$ or area under the curve of representing the adhered fraction over time (expressed in the form of the amount of adhered marker with respect to time) was evaluated by the trapezoid method to $t_z$ (the last sampling point) and allows quantifying the intensity of the bioadhesive phenomenon. Finally, $MRT_{adh}$ is the mean residence time of the adhered fraction of nanoparticles and it allows evaluating the relative duration of adhesive interactions, using the last sampling point as the limit.

Figure 10:
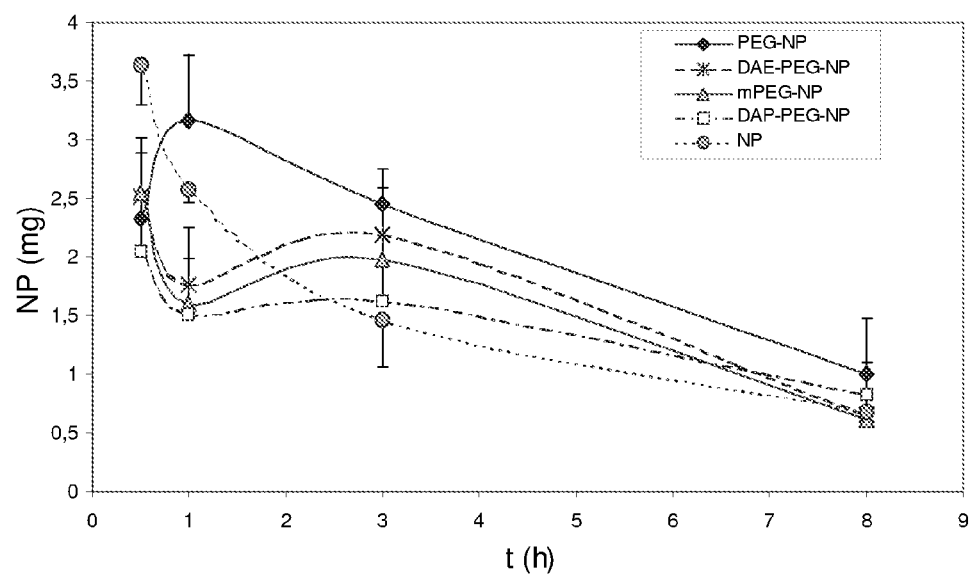
FIG. 10 shows the bioadhesion curves (NP, mg) of the different pegylated nanoparticles in the entire gastrointestinal tract after the oral administration of a single dose of 10 mg. t: time in hours.

FIG. 10 shows the bioadhesive profiles of the pegylated nanoparticles in the complete gastrointestinal tract for 8 hours. All the pegylated nanoparticles show bioadhesive profiles that are different from the profile of the non-modified particles (NP). The maximum bioadhesion of NP occurs 30 minutes after its oral administration and decreases quickly thereafter. In contrast, the pegylated nanoparticles generally have less initial ability to develop bioadhesive interactions. However, the adhesive ability is maintained for at least 3 hours. Therefore 3 hours after their administration, the amount of nanoparticles adhered to the gastrointestinal mucosa ranges between 25% of the administered dose for PEG-NP and 16% for DAP-PEG-NP, in all cases greater than the control (NP). On the other hand, the profile obtained for PEG-NP is particularly interesting. These nanoparticles show maximum adhesion 1 hour after their administration (about 32% of the dose) and 3 hours after their administration, the levels of particles adhered to the mucosa are similar to initial levels. In the case of the remaining pegylated nanoparticles, their initial adhesion is maintained for at least 3 hours.

The bioadhesive parameters can provide more details regarding the adhesive properties of the nanoparticles (Table 10). As previously stated, the initial ability of the pegylated nanoparticles to interact with the mucosa ($Q_{max}$) is lower that it is for the non-coated particles (NP). However, the bioadhesion area under the curve ($AUC_{adh}$) of the pegylated nanoparticles is higher; this means that the adhesive intensity is greater. This phenomenon is particularly observed in the case of PEG-NP, where $AUC_{adh}$ is 1.6-times greater than for NP. Furthermore, all the pegylated nanoparticle formulations have a lower degree of elimination of the adhered fraction ($k_{adh}$) and a longer residence time ($MRT_{adh}$) in comparison with the non-coated particles. Therefore, the DAP-PEG-NP show slower elimination of the adhered fraction than for conventional particles, suggesting the long-lasting bioadhesive potential of these nanoparticles. It is observed that all pegylated nanoparticles show a long residence time ($MRT_{adh}$) in the gastrointestinal tract. With respect to the mean residence time of the adhered fraction ($MRT_{adh}$), it is particularly interesting that all the pegylated nanoparticles show a significantly greater mean residence time than NP. Therefore, these nanoparticles show residence times comprised between 17 and 48 minutes greater than conventional particles.

TABLE 10

Bioadhesion parameters of the pegylated nanoparticles calculated according to their distribution in the complete gastrointestinal tract over time.

| Nanoparticles | $AUC_{adh}$ (mg h) | MRT (h) | $k_{adh}$ (h$^{-1}$) | $Q_{max}$ (mg) |
|---|---|---|---|---|
| NP | 11.83 ± 2.0 | 2.77 | 0.21 ± 0.01 | 3.64 ± 0.34 |
| PEG-NP | 16.19 ± 2.29 | 3.11 | 0.17 ± 0.01 | 3.16 ± 0.57 |
| mPEG-NP | 12.91 ± 6.84 | 3.10 | 0.16 ± 0.05 | 2.55 ± 1.17 |
| DAE-PEG-NP | 13.49 ± 1.76 | 3.05 | 0.17 ± 0.02 | 2.51 ± 0.50 |
| DAP-PEG-NP | 10.90 ± 5.04 | 3.57 | 0.14 ± 0.10 | 2.05 ± 0.47 |

Example 7

Viewing the Pegylated Nanoparticles in the Gastrointestinal Mucosa

The pegylated nanoparticles are viewed in the gastrointestinal mucosa by means of fluorescence and optical microscopy. To that end, the pegylated nanoparticles were marked with fluorescent molecules such as rhodamine B isothiocyanate (RBITC) and fluorescein isothiocyanate (FITC). After the oral administration in rats, different portions of the intestine are collected and washed with saline phosphate buffer (pH=7.4; 0.15M), as described above.

In the first case, the segments of the intestine (containing the nanoparticles marked with RBITC) are fixed in Tissue-Tek® O.C.T. medium (Sakura, Holland) and are frozen by means of dry ice and 2-methyl butane. The segments are then cut into 5 μm sections in a cryostat (Leica, Germany) at low temperature (−22° C.). The obtained sections are placed on a slide coated with poly-L-lysine (Sigma, Spain) and observed under a fluorescein microscope (Olympus CH-40, Japan).

On the other hand, the intestinal segments (containing nanoparticles marked with FITC) are fixed in a formalin solution (4%) for 24 hours. After the fixing, the tissues are included in paraffin and then cut into 3 μm sections. These sections are placed on a slide coated with Vectabond (Vector Labs, U.S.A.). Then the obtained sections are deparaffinized, rehydrated and endogenous peroxydase is blocked by means of adding a hydrogen peroxide solution (3%) for 10 minutes. Then the supports are washed with distilled water (5 min), placed in citrate buffer (pH=6.0; 0.01M), heated in a microwave (15 minutes at maximum power and 15 minutes at minimum power), washed with water and finally with Tris saline buffer (TBS) (pH=7.36; NaCl 0.5M; 0.05M). To prevent non-specific marking, the sections are incubated with normal goat serum (1:20, DAKO, U.S.A.) at room temperature for 30 minutes and then with the specific anti-serum (1:100 monoclonal anti-FITC, M0878, DAKO, U.S.A.) at 4° C. for 24 hours. After washing with Tris saline buffer (TBS), the samples are incubated with goat anti-mouse Ig secondary antibody coupled to Dextrane marked with peroxydase (room temperature, 30 minutes). The samples are washed with TBS buffer and the peroxydase activity is developed with a diaminobenzidine solution. The sections are weakly contrasted with hematoxylin, dehydrated and mounted in DPX. The samples are finally viewed under an optical microscope (Nicon Eclipse E 800M, Japan).

Figure 11:
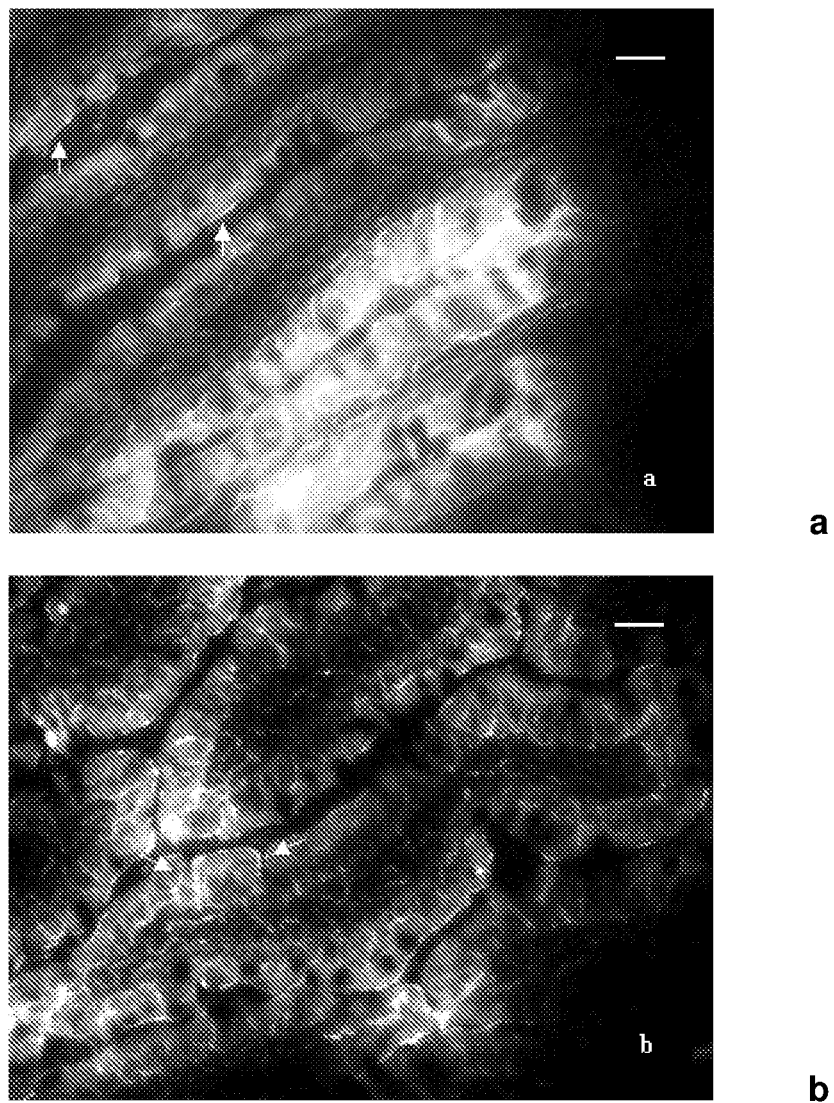
FIG. 11 shows fluorescence microscopy images of a portion of the ileum 2 hours after the oral administration of 10 mg of pegylated nanoparticles with PEG 2000 (PEG-NP). a) ileum villi: the arrows show the apical compartment of the epithelium; b) epithelial cells: the arrows show the fluorescence between the enterocytes. The scale presents 20 μm.

FIG. 11 shows the presence of PEG-NP in the small intestine epithelial cells. The particles are generally located in the apical compartment of the cells (FIG. 11 a), although certain fractions which have penetrated between cells of the intestinal epithelium can be observed (FIG. 11 b).

Figure 12:
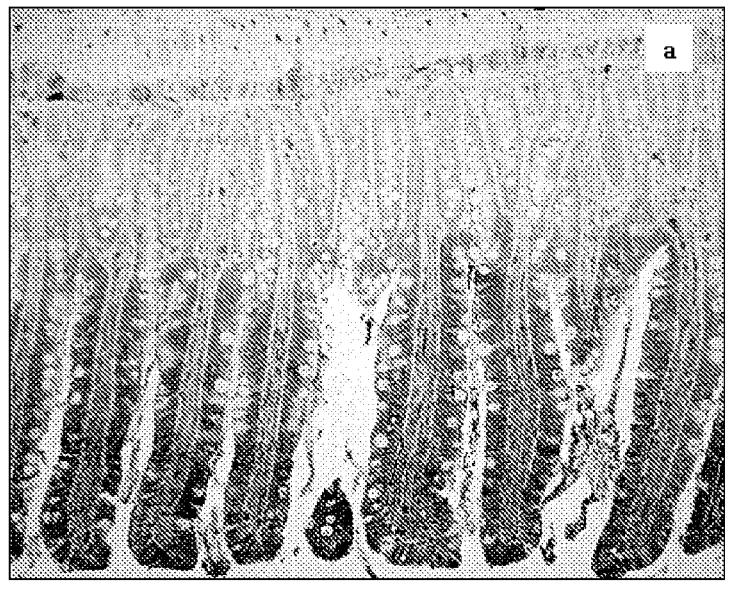
FIG. 12 shows optical microscopy images of the ileum segment 2 hours after the oral administration of 10 mg of pegylated nanoparticles with PEG 2000 (PEG-NP). a) general view (magnification of 135) and b) enlarged detail (magnification of 530). L: lumen; E: enterocytes; GC: mucus generating cells; dark arrows: enterocyte nuclei; white arrows: blood capillaries in the submucosa.
Figure 12:
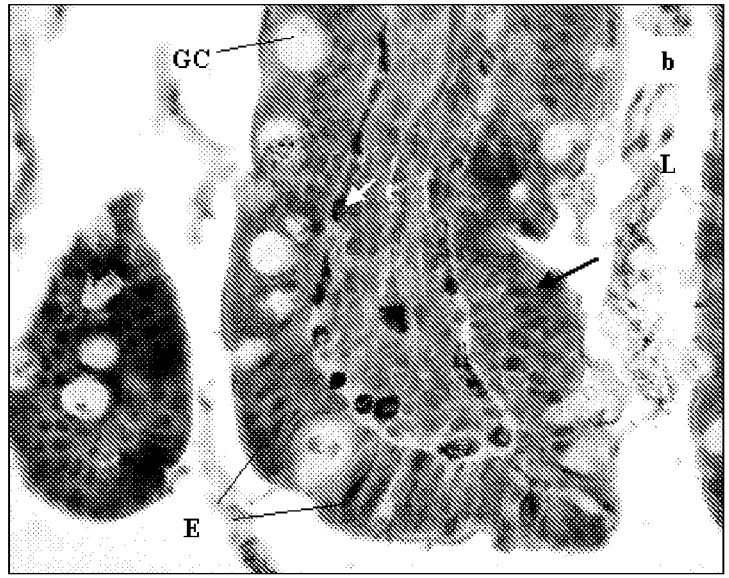

Intensive penetration of the nanoparticles in the enterocytes can be observed by optical microscopy (FIG. 12). As with fluorescein microscopy, distribution in the apical compartment of the cells is observed. On the other hand, FIG. 12 b also shows a distribution in the basolateral compartment. It is observed that some of the nuclei of the cells include the marker or marked nanoparticles, which allows assuming that the use of these nanoparticles can be interesting to promote the delivery to the nucleus of different biologically active molecules.

Figure 13:
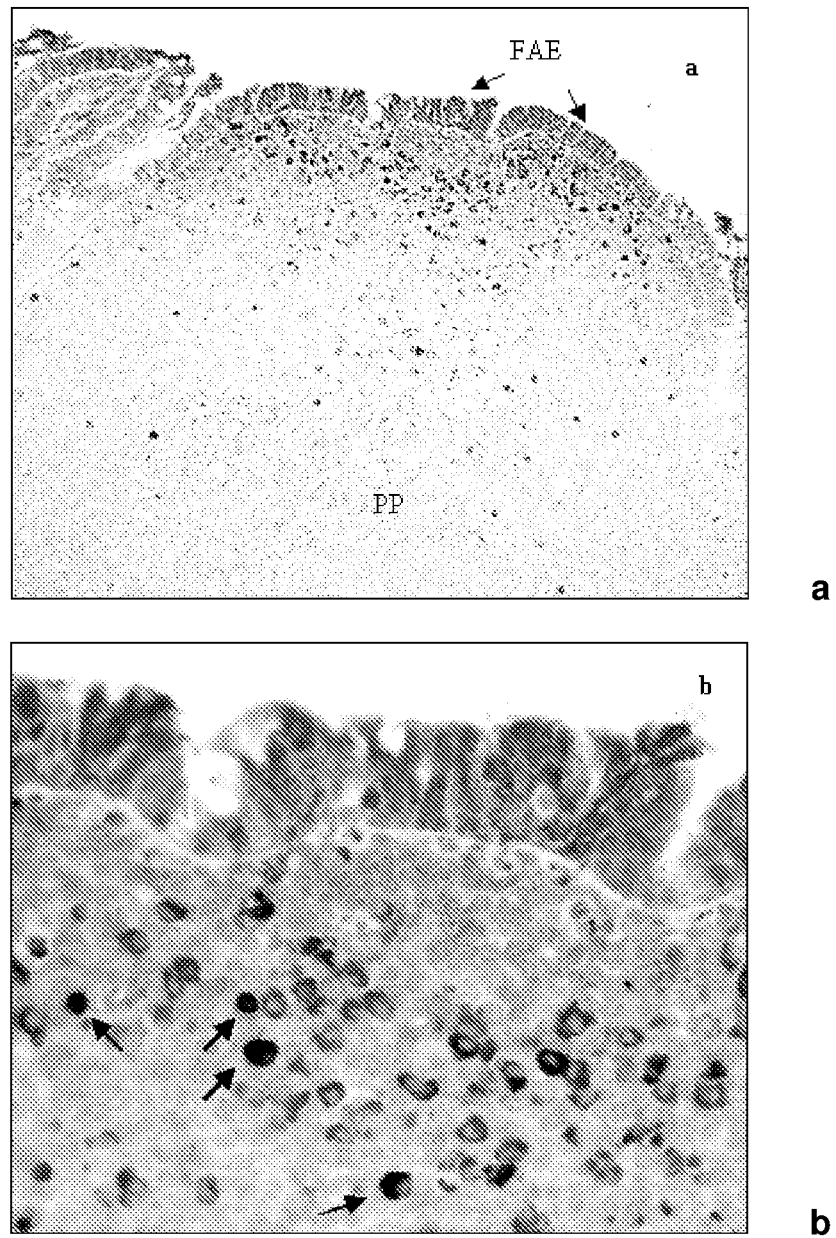
FIG. 13 shows the location of PEG-NP in an ileum Peyer's patch, two hours after the oral administration of 10 mg of the nanoparticles. a) general view of the Peyer's patch (magnification of 135); b) enlarged detail (magnification of 530); PP—Peyer's patch; FAE—follicle-associated epithelium; dark arrows: Peyer's patch dome cells where the nanoparticles would be included.

Finally, FIG. 13 shows the distribution of these systems in Peyer's patch cells. The observation that these nanoparticles seem to be concentrated in the area known as the "dome" of the Peyer's patch is particularly interesting. The dome is characterized in that it is the area where cells of the monocyte-macrophage system accumulate. This allows asserting the interest of these pegylated nanoparticles for the development of oral vaccines and in immunotherapy.

The invention claimed is:

1. Oral pegylated nanoparticles for carrying biologically active molecules comprising a pegylated biodegradable polymer, said biodegradable polymer being a vinyl methyl ether and maleic anhydride (PVM/MA) copolymer, said pegylated nanoparticles having increased intestinal mean residence time as compared with nanoparticles of PVM/MA lacking PEG, and wherein said pegylated nanoparticles are pegylated with a polyethylene glycol (PEG) or a derivative thereof having a molecular weight between 1,500 and 10,000 Da.

2. Nanoparticles according to claim 1, wherein the copolymer has a molecular weight between 200 and 2000 KDa.

3. Nanoparticles according to claim 1, wherein the weight ratio between polyethylene glycol and the biodegradable polymer is 1:2-4.

4. Nanoparticles according to claim 1, wherein the biologically active molecule is a protein or peptide.

5. Nanoparticles according to claim 1, wherein the biologically active molecule is selected from the group consisting of DNA, RNA, nucleosides, nucleotides, oligonucleotides or polynucleotides.

6. Nanoparticles according to claim 1, wherein the biologically active molecule is an anti-tumor agent or an antigen for tumors.

7. Nanoparticles according to claim 1, wherein the biologically active molecule is a protective agent of the central nervous system or a glucocorticoid.

8. Nanoparticles according to claim 1, wherein the biologically active molecule is an antigen for vaccination or an allergen for immunotherapy.

9. A pharmaceutical composition comprising the pegylated nanoparticles of claim 1, further comprising an excipient, carrier or adjuvant.

10. A pharmaceutical composition according to claim 9 adapted for administration by a route providing access to a mucosa.

11. A pharmaceutical composition according to claim 10 for oral administration.

12. A method of orally administering a therapeutic agent to a subject, said method comprising delivering the therapeutic agent to said subject in the nanoparticle of claim 1.

13. A lyophilizate comprising pegylated nanoparticles according to claim 1.

14. A process of preparing the pegylated nanoparticles of claim 1 said process comprising a first step of simultaneous incubation of the biodegradable polymer and polyalkylene glycol in an organic solvent, followed by a second step of desolvating the polymer with a hydroalcoholic solution.

15. A process according to claim 14, characterized by at least one of the following:
(a) removal of organic solvents and/or purification;
(b) addition of an active molecule during the simultaneous incubation of the biodegradable polymer and the polyalkylene glycol in an organic solvent; and
(c) an additional lyophilization, optionally in the presence of a cryoprotective agent.

16. A process according to claim 15, wherein the active molecule is added in the step of simultaneous incubation of the biodegradable polymer and the polyalkylene glycol in an organic solvent.

17. A process according to claim 15, comprising lyophilization step in the presence of a cryoprotective agent selected from the group consisting of sucrose and mannitol.

18. A process according to claim 15, wherein said copolymer has a molecular weight between 100 and 2400 kDa.

* * * * *